(12) United States Patent
Pease et al.

(10) Patent No.: US 7,153,964 B2
(45) Date of Patent: *Dec. 26, 2006

(54) PYRIMIDINE COMPOUNDS

(75) Inventors: Elizabeth Janet Pease, Macclesfield (GB); Gloria Anne Breault, Macclesfield (GB); Jeffrey James Morris, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 413 days.

This patent is subject to a terminal disclaimer.

(21) Appl. No.: 10/220,139

(22) PCT Filed: Feb. 26, 2001

(86) PCT No.: PCT/GB01/00782

§ 371 (c)(1),
(2), (4) Date: Aug. 28, 2002

(87) PCT Pub. No.: WO01/64654

PCT Pub. Date: Sep. 7, 2001

(65) Prior Publication Data

US 2003/0149064 A1 Aug. 7, 2003

(30) Foreign Application Priority Data

Mar. 1, 2000 (GB) .................................. 0004888.4

(51) Int. Cl.
*C07D 239/47* (2006.01)
*C07D 239/48* (2006.01)
*C07D 471/04* (2006.01)
*C07D 471/14* (2006.01)
*A61K 31/437* (2006.01)
*A61P 35/00* (2006.01)

(52) U.S. Cl. ...................... 544/321; 544/324; 544/325; 514/272; 514/275

(58) Field of Classification Search ............... 544/321, 544/324, 325; 514/272, 275
See application file for complete search history.

(56) References Cited

U.S. PATENT DOCUMENTS

| | | | | |
|---|---|---|---|---|
| 3,432,493 | A * | 3/1969 | Short ........................... | 544/312 |
| 4,983,608 | A | 1/1991 | Effland et al. ............... | 514/216 |
| 5,516,775 | A | 5/1996 | Zimmermann et al. .. | 514/224.2 |
| 5,521,184 | A | 5/1996 | Zimmermann ............... | 514/252 |
| 5,610,303 | A | 3/1997 | Kimura et al. ............... | 544/326 |
| 5,739,143 | A | 4/1998 | Adams et al. ............... | 514/275 |
| 5,859,041 | A | 1/1999 | Liverton et al. ............. | 514/396 |
| 6,632,820 | B1 * | 10/2003 | Breault et al. ............... | 514/256 |
| 6,838,464 | B1 * | 1/2005 | Pease et al. .................. | 514/272 |

FOREIGN PATENT DOCUMENTS

| | | |
|---|---|---|
| CA | 2231765 | 9/1998 |
| EP | 0 363 002 | 4/1990 |
| EP | 0 379 806 B1 | 8/1990 |
| EP | 0 564 409 B1 | 10/1993 |
| EP | 0 945 443 A | 9/1999 |
| WO | 91/18887 | 12/1991 |
| WO | 92/20642 | 11/1992 |
| WO | 95/09847 | 4/1995 |
| WO | 95/09851 | 4/1995 |
| WO | 95/09852 | 4/1995 |
| WO | 95/09853 | 4/1995 |
| WO | 95/15952 | 6/1995 |
| WO | 96/05177 | 2/1996 |

(Continued)

OTHER PUBLICATIONS

Wolft Manfred E. "Burger's Medicinal Chemistry, 5ed, Part 1", John Wiley & Sons, 1995, pp. 975-977.*

(Continued)

*Primary Examiner*—Venkataraman Balasubramanian
(74) *Attorney, Agent, or Firm*—Morgan Lewis & Bockius LLP

(57) ABSTRACT

Pyrimidine derivatives of formula (I) wherein: $Qh_1$ and $Q_2$ are independently selected from aryl or carbon linked heteroaryl optionally substituted as defined within; and one of $Q_1$ and $Q_2$ or both $Q_1$ and $Q_2$ is substituted on a ring carbon by one group selected from sulphamoyl, N—($C_{1-4}$alkyl)sulphamoyl (optionally substituted by halo or hydroxy), N,N-di-($C_{1-4}$alkyl)sulphamoyl (optionally substituted by halo or hydroxy), $C_{1-4}$alkylsulphonyl (optionally substituted by halo or hydroxy) or a substituent of the formula (Ia) or (Ia'): wherein $Q_1$, $Q_2$, G, $R^1$, Y, Z, $Q_3$, n and m are as defined within; and pharmaceutically acceptable salts and in vivo hydrolysable esters thereof are described. Processes for their manufacture, pharmaceutical compositions and their use as cyclin-dependent serine/threonine kinase (CDK) inhibitors are also described

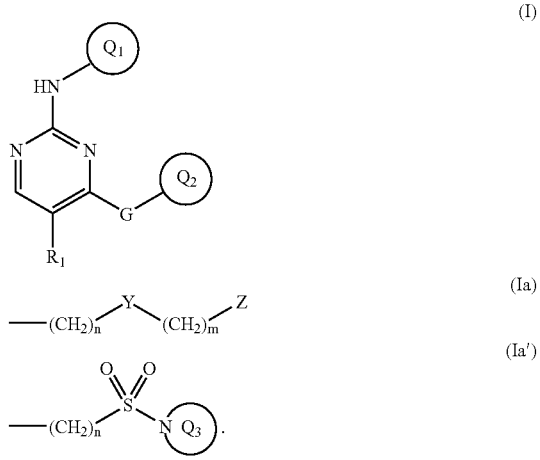

12 Claims, No Drawings

FOREIGN PATENT DOCUMENTS

| WO | 96/28427 | | 9/1996 |
|---|---|---|---|
| WO | 96/40143 | | 12/1996 |
| WO | 97/19065 | A | 5/1997 |
| WO | 97/35856 | | 10/1997 |
| WO | 97/40017 | | 10/1997 |
| WO | 97/44326 | | 11/1997 |
| WO | 97/47618 | | 12/1997 |
| WO | 98/11095 | | 3/1998 |
| WO | 98/16230 | | 4/1998 |
| WO | 98/18782 | | 5/1998 |
| WO | 98/25619 | | 6/1998 |
| WO | 98/33798 | | 8/1998 |
| WO | 98/41512 | | 9/1998 |
| WO | 98/54093 | | 12/1998 |
| WO | 98/56788 | | 12/1998 |
| WO | 99/01136 | | 1/1999 |
| WO | 99/32121 | | 1/1999 |
| WO | 99/18096 | | 4/1999 |
| WO | 99/18942 | | 4/1999 |
| WO | 99/31073 | | 6/1999 |
| WO | 99/41253 | | 8/1999 |
| WO | 99/50250 | | 10/1999 |
| WO | 00/12485 | A | 3/2000 |
| WO | 00/12486 | | 3/2000 |
| WO | 00/17202 | | 3/2000 |
| WO | 00/17203 | | 3/2000 |
| WO | 00/21926 | | 4/2000 |
| WO | 00/25780 | | 5/2000 |
| WO | 00/26209 | | 5/2000 |
| WO | 00/39101 | A | 7/2000 |
| WO | 00/44750 | | 8/2000 |
| WO | 00/49018 | | 8/2000 |
| WO | 00/53595 | | 9/2000 |
| WO | 00/55161 | | 9/2000 |
| WO | 00/59892 | A | 10/2000 |
| WO | 00/78731 | A1 | 12/2000 |
| WO | 01/14375 | | 3/2001 |
| WO | 01/29009 | A1 | 4/2001 |
| WO | 01/30778 | A1 | 5/2001 |
| WO | 01/37835 | A1 | 5/2001 |
| WO | 01/47897 | A1 | 7/2001 |
| WO | 01/47921 | A1 | 7/2001 |
| WO | 01/60816 | A1 | 8/2001 |
| WO | 01/64653 | A1 | 9/2001 |
| WO | 01/64655 | A1 | 9/2001 |
| WO | 01/64656 | A1 | 9/2001 |
| WO | 01/72717 | A1 | 10/2001 |
| WO | 02/04429 | A1 | 1/2002 |
| WO | 02/20512 | A1 | 3/2002 |
| WO | WO 02/20512 | | 3/2002 |

OTHER PUBLICATIONS

Banker, G.S. et al, "Modern Pharmaceutices, 3ed.", Marcel Dekker, New York 1996, 451 and 596.*

Egyptian Journal of Chemistry 29(2), 247-251, 1987, CA 109:170352, 1988.*

Tan et al., Seminars in Oncology 293) Supple,ement 11, 77-85,2002.*

Kornberg, Head Neck 20(8): 745-52, 1998.*

Cecil Textbook of Medicine, edited Bennet, J.C., and Plum F., 20th edition,vol. 1, 1004-1010, 1996.*

El-Kerdawy et al., "2,4-bis(substituted) 5-nitropyrimindines of expected diuretic action", Egypt. J. Chem., 1987, Volume Date 1986, 29(2), pp. 247-251, XP000999986, see Table 1.

Ghosh, "2,4-Bis(arylamino)-6-methylpyrimidines as antimicrobial agents", J. Indian Chem. Soc., 1981, 58(5), pp. 512-213.

U.S. Appl. No. 09/763,705, filed Feb. 26, 2001, Breault et al.

U.S. Appl. No. 09/763,681, filed Feb. 26, 2001, Breault et al.

U.S. Appl. No. 09/868,602, filed Jun. 20, 2001, Bradbury et al.

U.S. Appl. No. 09/914,788, filed Sep. 5, 2001, Breault et al.

U.S. Appl. No. 09/958,077, filed Oct. 4, 2001, Breault.

U.S. Appl. No. 10/203,154, filed Aug. 6, 2002, Pease et al.

U.S. Appl. No. 10/203,025, filed Aug. 5, 2002, Pease et al.

U.S. Appl. No. 10/203,549, filed Aug. 8, 2002, Pease et al.

U.S. Appl. No. 10/069,019, filed Feb. 21, 2002, Thomas et al.

U.S. Appl. No. 10/239,790, filed Sep. 25, 2002, Thomas et al.

U.S. Appl. No. 10/332,275, filed Jan 7, 2003, Thomas et al.

"2,4-Bis (Substituted)-5-Nitropyrimidines of Expected Diuiretic Action" by M. El-Kerdawy et al., Egypt. J. Chem. vol. 29, No. 2, pp. 247-251 (1986).

Boschelli et al., Synthesis and Tyrosine Kinase Inhibitory Activity of a Series of 2-Amino-8-$H$-pyrido[2,3-$d$]pyrimidines: Identifidation of Potent, Selective Platelet-Derived Growth Factor Receptor Tyrosine Kinase Inhibitors, J. Med. Chem., vol. 41, 1998, pp. 4365-4377.

Deady et al., "Reactions of some Quinazoline Compounds with Ethoxymethylenemalonic Acid Derivatives", J. Heterocyclic Chem., vol. 26, 1989, pp. 161-168.

Donnellan et al., "Cyclin E in human cancers", FASEB Journal, 13, 1999, pp. 773-780.

Fiziol Akt Veshchestva, 1975, vol. 7, pp. 68-72.

Ghosh et al.; "2,4-Bis(arylamino)-5-methylpyrimidines as Antimicrobial Agents"; J. Med. Chem., 1967, vol. 10, No. 5, pp. 974-975.

Ghosh, "2,4-Bis(arylamino)-6-methylpyrimidines as an antimicrobial agents", Chemical Abstract No. 97712f, vol. 95, 1981, pp. 648.

Schmidt et al.; "A Convenient Synthesis of 2-substituted 4-Amino-5-pyrimidinecarbonitriles"; J. Heterocycle Chem., 1997, vol. 24, No. 5, pp. 1305-1307.

Zimmermann et al., Phenylamino-Pyrimidine (PAP) Derivatives: A New Class of Potent and Selective Inhibitors of Protein Kinase C (PKC), Arch. Pharm. Pharm. Med. Chem., vol. 329, 1996, pp. 371-376.

* cited by examiner

PYRIMIDINE COMPOUNDS

The invention relates to pyrimidine derivatives, or pharmaceutically acceptable salts or in vivo hydrolysable esters thereof, which possess cell-cycle inhibitory activity and are accordingly useful for their anti cell proliferation (such as anti-cancer) activity and are therefore useful in methods of treatment of a warm-blooded animal, such as man. The invention also relates to processes for the manufacture of said pyrimidine derivatives, to pharmaceutical compositions containing them and to their use in the manufacture of medicaments or use in the production of an anti-cell-proliferation effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppresser gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

The present invention is based on the discovery that certain 2,4-pyrimidine compounds surprisingly inhibit the effects of cell cycle kinases showing selectivity for CDK2, CDK4 and CDK6, and thus possess anti-cell-proliferation properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

According to the invention there is provided a pyrimidine derivative of the formula (I):

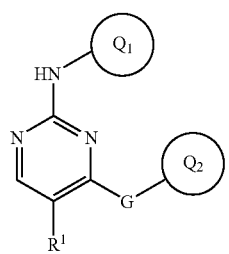

wherein:

$Q_1$ and $Q_2$ are independently selected from aryl or carbon linked heteroaryl; and one of $Q_1$ and $Q_2$ or both $Q_1$ and $Q_2$ is substituted on a ring carbon by one group selected from sulphamoyl, N—($C_{1-4}$alkyl)sulphamoyl (optionally substituted by halo or hydroxy), N,N-di-($C_{1-4}$alkyl)sulphamoyl (optionally substituted by halo or hydroxy), $C_{1-4}$alkylsulphonyl (optionally substituted by halo or hydroxy) or a substituent of the formula (Ia) or (Ia'):

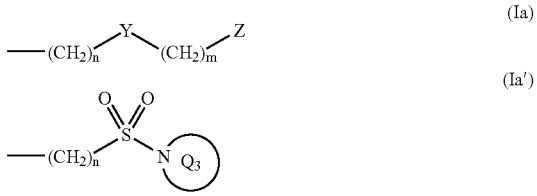

wherein:
Y is —NHS(O)$_2$—, —S(O)$_2$NH— or —S(O)$_2$—;
Z is $R^a$O—, $R^bR^cN$—, $R^dS$—, $R^eR^fNNR^g$—, $C_{3-8}$cycloalkyl, phenyl or a heterocyclic group;

wherein said phenyl, $C_{3-8}$cycloalkyl or heterocyclic group are optionally substituted on a ring carbon by one or more groups selected from $R^h$; and wherein if said heterocyclic group contains an —NH— moiety that nitrogen may be optionally substituted by a group selected from $R^i$;

$R^a$, $R^b$, $R^c$, $R^d$, $R^e$, $R^f$ and $R^g$ are independently selected from hydrogen, $C_{1-4}$alkyl, $C_{2-4}$alkenyl, phenyl, heterocyclic group and $C_{3-8}$cycloalkyl; wherein said $C_{1-4}$alkyl, $C_{2-4}$alkenyl and $C_{3-8}$cycloalkyl are optionally substituted by one or more groups selected from $R^j$;

n is 0 or 1;
m is 1, 2 or 3, in addition m may be 0 when Z is $C_{3-8}$cycloalkyl, phenyl or a heterocyclic group;

$Q_3$ is a nitrogen linked heterocycle; wherein said heterocycle is optionally substituted on a ring carbon by one or more groups selected from $R^1$; and wherein if said heterocyclic group contains an —NH— moiety that nitrogen may be optionally substituted by a group selected from $R^m$ G is —O—, —S— or —NR$^2$—;

$R^2$ is selected from hydrogen, $C_{1-6}$alkyl, $C_{3-6}$alkenyl and $C_{3-6}$alkynyl; wherein said $C_{1-6}$alkyl, $C_{3-6}$alkenyl and $C_{3-6}$alkynyl are optionally substituted by one or more groups selected from $R^n$;

$R^1$ is selected from hydrogen, halo, hydroxy, nitro, amino, N—($C_{1-3}$alkyl)amino, N,N-di-($C_{1-3}$alkyl)amino, cyano, trifluoromethyl, trichloromethyl, $C_{1-3}$alkyl [optionally substituted by 1 or 2 substituents independently selected from halo, cyano, amino, N—($C_{1-3}$alkyl)amino, N,N-di-($C_{1-3}$alkyl)amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, mercapto, $C_{1-3}$alkylsulphanyl, carboxy and $C_{1-3}$alkoxycarbonyl;

$Q_1$ is optionally substituted on a ring carbon by one to four substituents independently selected from halo, mercapto, nitro, formyl, formamido, carboxy, cyano, amino, ureido, carbamoyl, $C_{1-4}$alkyl, $C_{2-4}$alkenyl, $C_{2-4}$alkynyl [wherein said $C_{1-4}$alkyl, $C_{2-4}$alkenyl and $C_{2-4}$alkynyl are optionally substituted by one or more groups selected from $R^o$], $C_{1-4}$alkanoyl, $C_{1-4}$alkoxycarbonyl, heterocyclic group, $C_{1-4}$alkylS(O)$_a$ wherein a is 0 or 1 [optionally substituted by hydroxy], N'—($C_{1-4}$alkyl)ureido, N',N'-di-($C_{1-4}$alkyl)ureido, N'—

($C_{1-4}$alkyl)-N—($C_{1-4}$alkyl)ureido, N',N'-di-($C_{1-4}$alkyl)-N—($C_{1-4}$alkyl)ureido, N—$C_{1-4}$alkylamino, N,N-di-($C_{1-4}$alkyl)amino, N—$C_{1-4}$alkylcarbamoyl, N,N-di-($C_{1-4}$alkyl)carbamoyl and $C_{1-4}$alkanoylamino;

and also independently, or in addition to, the above substituents, $Q_1$ may be optionally substituted by one to two substituents independently selected from aryl, $C_{3-8}$cycloalkyl and a heterocyclic group; wherein said aryl, $C_{3-8}$cycloalkyl or heterocyclic group may be optionally substituted on a ring carbon by one or more groups selected from $R^p$; and wherein if said heterocyclic group contains an —NH— moiety that nitrogen may be optionally substituted by a group selected from $R^q$;

and also independently, or in addition to, the above substituents, $Q_1$ may be optionally substituted by one $C_{1-4}$alkoxy or by one hydroxy substituent;

$Q_2$ is optionally substituted on a ring carbon by one to four substituents independently selected from halo, hydroxy, mercapto, nitro, formyl, formamido, carboxy, cyano, amino, ureido, carbamoyl, $C_{1-4}$alkyl, $C_{2-4}$alkenyl, $C_{2-4}$alkynyl, $C_{1-4}$alkoxy [wherein said $C_{1-4}$alkyl, $C_{2-4}$alkenyl, $C_{2-4}$alkynyl and $C_{1-4}$alkoxy are optionally substituted by one or more groups selected from $R^1$], $C_{1-4}$alkanoyl, $C_{1-4}$alkoxycarbonyl, heterocyclic group, $C_{1-4}$alkylS(O)$_a$ wherein a is 0 or 1 [optionally substituted by hydroxy], N'—($C_{1-4}$alkyl)ureido, N',N'-di-($C_{1-4}$alkyl)ureido, N'—($C_{1-4}$alkyl)-N—($C_{1-4}$alkyl)ureido, N',N'-di-($C_{1-4}$alkyl)-N—($C_{1-4}$alkyl)ureido, N—$C_{1-4}$alkylamino, N,N-di-($C_{1-4}$alkyl)amino, N—$C_{1-4}$alkylcarbamoyl, N,N-di-($C_{1-4}$alkyl)carbamoyl, $C_{2-4}$alkenyloxy, $C_{2-4}$alkynyloxy and $C_{1-4}$alkanoylamino;

and also independently, or in addition to, the above substituents, $Q_2$ may be optionally substituted by one to two substituents independently selected from aryl, $C_{3-8}$cycloalkyl or a heterocyclic group; wherein said aryl, $C_{3-8}$cycloalkyl or heterocyclic group may be optionally substituted on a ring carbon by one or more groups selected from $R^s$; and wherein if said heterocyclic group contains an —NH— moiety that nitrogen may be optionally substituted by a group selected from $R^t$;

$R^j$, $R^n$, $R^o$ and $R^r$ are independently selected from hydroxy, halo, amino, cyano, formyl, formamido, carboxy, nitro, mercapto, carbamoyl, sulphamoyl, N—$C_{1-4}$alkylamino, N,N-di-($C_{1-4}$alkyl)amino, $C_{1-4}$alkanoyl, $C_{1-4}$alkanoyloxy, $C_{1-4}$alkoxy, $C_{1-4}$alkoxycarbonyl, N—$C_{1-4}$alkylcarbamoyl, N,N-di-($C_{1-4}$alkyl)carbamoyl, $C_{1-4}$alkanoylamino, $C_{1-4}$alkylS(O)$_a$ wherein a is 0 to 2, $C_{1-4}$alkylsulphonylamino, N—($C_{1-4}$alkyl)sulphamoyl, N—($C_4$alkyl)$_2$sulphamoyl, N—($C_{1-4}$alkyl)carbamoyl, N—($C_{1-4}$alkyl)$_2$carbamoyl, phenyl, phenylthio, phenoxy, $C_{3-8}$Cycloalkyl and a heterocyclic group; wherein said phenyl, phenylthio, phenoxy, $C_{3-8}$cycloalkyl or heterocyclic group may be optionally substituted on a ring carbon by one or more groups selected from $R^u$; and wherein if said heterocyclic group contains an —NH— moiety that nitrogen may be optionally substituted by a group selected from $R^v$;

$R^h$, $R^k$, $R^p$, $R^s$ and $R^u$ are independently selected from hydroxy, halo, amino, cyano, formyl, formamido, carboxy, nitro, mercapto, carbamoyl, sulphamoyl, $C_{1-4}$alkyl [optionally substituted by one or more groups selected from halo, cyano, amino, N—$C_{1-4}$alkylamino, N,N-di-($C_{1-4}$alkyl)amino or hydroxy], $C_{2-4}$alkenyl [optionally substituted by one or more groups selected from halo], $C_{2-4}$alkynyl, N—$C_{1-4}$alkylamino, N,N-di-($C_{1-4}$alkyl)amino, $C_{1-4}$alkanoyl, $C_{1-4}$alkanoyloxy, $C_{1-4}$alkoxy [optionally substituted by one or more groups selected from halo], $C_{1-4}$alkoxycarbonyl, N—$C_{1-4}$alkylcarbamoyl, N,N-di-($C_{1-4}$alkyl)carbamoyl, $C_{1-4}$alkanoylamino, $C_{1-4}$alkylS(O)$_a$ wherein a is 0 to 2, $C_{1-4}$alkylsulphonylamino, N—($C_{1-4}$alkyl)sulphamoyl, N—($C_{1-4}$alkyl)$_2$sulphamoyl, phenyl, $C_{3-8}$cycloalkyl and a heterocyclic group; and $R^1$, $R^q$, $R^t$ and $R^v$ are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl; or a pharmaceutically acceptable salt or in vivo hydrolysable ester thereof.

"Aryl" is a fully or partially unsaturated, mono or bicyclic carbon ring that contains 4–12 atoms. Preferably "aryl" is a monocyclic ring containing 5 or 6 atoms or a bicyclic ring containing 9 or 10 atoms. More preferably "aryl" is phenyl, naphthyl, tetralinyl or indanyl. Particularly "aryl" is phenyl, naphthyl or indanyl. More particularly "aryl" is phenyl.

A "carbon linked heteroaryl" is a fully unsaturated, 5- or 6-membered monocyclic ring or 9- or 10-membered bicyclic ring of which at least one atom is chosen from nitrogen, sulphur or oxygen. This ring is linked via a carbon atom to the —NH— (for $Q_1$) or G (for $Q_2$). Preferably "carbon linked heteroaryl" is furanyl, thienyl, pyrrolyl, oxazolyl, isoxazolyl, thiazolyl, isothiazolyl, imidazolyl, pyrazolyl, furazanyl, triazolyl, thiadiazolyl, pyridyl, pyrimidyl, pyrazinyl, pyridazinyl, triazinyl, indolyl, quinolyl or benzimidazolyl. More preferably "carbon linked heteroaryl" is pyridyl, thiazolyl or pyrazolyl. Particularly "carbon linked heteroaryl" is pyridyl.

A "heterocyclic group" is a saturated, partially saturated or unsaturated, mono or bicyclic ring containing 4–12 atoms of which at least one atom is chosen from nitrogen, sulphur or oxygen, which may, unless otherwise specified, be carbon or nitrogen linked, wherein a —$CH_2$— group can optionally be replaced by a —C(O)—, and a ring sulphur atom may be optionally oxidised to form S-oxide(s). Preferably a "heterocyclic group", is pyrrolidinyl, morpholino, piperidyl, pyridyl, pyranyl, pyrrolyl, isothiazolyl, indolyl, quinolyl, thienyl, furyl, 1,3-benzodioxolyl, thiadiazolyl, piperazinyl, isoxazolyl, thiazolyl, thiazolidinyl, pyrrolidinyl, thiomorpholino, pyrazolyl, pyrrolinyl, homopiperazinyl, tetrahydropyranyl, imidazolyl, pyrimidyl, pyrazinyl, pyridazinyl, isoxazolyl, 4-pyridone, 1-isoquinolone, 2-pyrrolidone, 4-thiazolidone, imidazo[1,2-a]pyridine or 3-aza-8-oxabicyclo[3,2,1]hexane. More preferably a "heterocyclic group" is pyrrolidinyl, morpholino, piperidyl, isoxazolyl, thiadiazolyl, thiazolyl, pyridyl, indolyl, thienyl, furyl, piperazinyl, thiomorpholino, pyrazolyl, imidazolyl, 2-pyrrolidone, imidazo[1,2-a]pyridine or 3-aza-8-oxabicyclo[3,2,1]hexane. Particularly a "heterocyclic group" is morpholino, isoxazolyl, thiadiazolyl, thiazolyl or pyridyl.

A "nitrogen linked heterocycle" is a saturated, partially saturated or fully unsaturated, mono or bicyclic ring containing 4–12 atoms, one atom of which is a nitrogen atom (attached to form an amide as shown) and the other atoms are either all carbon atoms or they are carbon atoms and 1–3 heteroatoms chosen from nitrogen, sulphur or oxygen, wherein a —$C_{1-2}$— group can optionally be replaced by a —C(O)— and a ring sulphur atom may be optionally oxidised to form the S-oxides. It will be appreciated that in forming this nitrogen link, the nitrogen atom is not quaternised, i.e. a neutral compound is formed. Preferably "nitrogen linked heterocycle" is pyrrol-1-yl, pyrrolin-1-yl, pyrrolidin-1-yl, imidazol-1-yl, imidazolin-1-yl, imidazolidin-1-yl, pyrazol-1-yl, pyrazolin-1-yl, pyrazolidin-1-yl, triazol-1-yl, piperidin-1-yl, piperazin-1-yl, morpholino, thiomorpholino, indol-1-yl, indolidin-1-yl or benzimidazol-1-yl. More preferably "nitrogen linked heterocycle" is piperidin-1-yl.

In this specification the term "alkyl" includes both straight and branched chain alkyl groups but references to individual alkyl groups such as "propyl" are specific for the straight chain version only. An analogous convention applies to other generic terms. "Halo" is fluoro, chloro, bromo and iodo.

Examples of $C_{2-4}$alkenyl are vinyl and allyl; examples of $C_{2-6}$alkenyl are $C_{3-5}$alkenyl, vinyl and allyl; examples of $C_{3-6}$alkenyl are $C_{3-5}$alkynyl and allyl; an example of $C_{3-6}$alkynyl is propyn-2-yl; examples of $C_{2-4}$alkynyl are ethynyl and propyn-2-yl; examples of $C_{2-6}$alkynyl are ethynyl and propyn-2-yl; examples of $C_{1-4}$alkanoyl are acetyl and propionyl; examples of $C_{1-4}$alkoxycarbonyl are $C_{1-3}$alkoxycarbonyl, methoxycarbonyl, ethoxycarbonyl, propoxycarbonyl and tert-butoxycarbonyl; examples of $C_{1-4}$alkylene are methylene, ethylene and propylene; examples of $C_{1-4}$alkyl are $C_{1-3}$alkyl, methyl, ethyl, propyl, isopropyl, butyl, isobutyl, sec-butyl and tert-butyl; examples of $C_{1-6}$alkyl are methyl, ethyl, propyl, isopropyl, butyl, isobutyl, sec-butyl, tert-butyl and 3-methylbutyl; examples of $C_{1-4}$alkoxy are $C_{1-3}$alkoxy, methoxy, ethoxy, propoxy, isopropoxy and butoxy; an example of $C_{2-4}$alkenyloxy is allyloxy; an example of $C_{2-4}$alkynyloxy is propynyloxy; examples of $C_{1-4}$alkylS(O)$_a$ wherein a is 0 or 1 are $C_{1-3}$alkylsulphanyl, methylthio, ethylthio, propylthio, methylsulphinyl, ethylsulphinyl and propylsulphinyl; examples of $C_{1-4}$alkylS(O)$_2$ wherein a is 0 to 2 are methylthio, ethylthio, propylthio, methylsulphinyl, ethylsulphinyl, propylsulphinyl, mesyl, ethylsulphonyl and propylsulphonyl; examples of $C_{1-4}$alkylsulphonyl are mesyl and ethylsulphonyl; examples of N—$C_{1-4}$alkylcarbamoyl are N-methylcarbamoyl, N-ethylcarbamoyl and N-propylcarbamoyl; examples of N,N-di-($C_{1-4}$alkyl)-carbamoyl are N,N-dimethylcarbamoyl, N-ethyl-N-methylcarbamoyl and N,N-diethylcarbamoyl; examples of N—$C_{1-4}$alkylamino are N—($C_{1-3}$alkyl)amino, methylamino, ethylamino and propylamino; examples of N,N-di-($C_{1-4}$alkyl)amino are N,N-di-($C_{1-3}$alkyl)amino, dimethylamino, N-ethyl-N-methylamino, diethylamino, N-methyl-N-propylamino and dipropylamino; examples of $C_{1-4}$alkanoylamino are acetamido, propionamido and butyramido; examples of $C_{3-8}$cycloalkyl are cyclopropyl, cyclopentyl and cyclohexyl; examples of $C_{1-4}$alkanoyl are acetyl and propionyl; examples of $C_{1-4}$alkanoyloxy are acetyloxy and propionyloxy; examples of N'—($C_{1-4}$alkyl)ureido are N'-methylureido and N'-ethylureido; examples of N',N'-di-($C_{1-4}$alkyl)ureido are N',N'-dimethylureido, N',N'-diisopropylureido and N'-methyl-N'-propylureido; examples of N'—($C_{1-4}$alkyl)-N—($C_{1-4}$alkyl)ureido are N'-methyl-N-ethylureido and N'-methyl-N-methylureido; examples of N',N'-di-($C_{1-4}$acyl)-N—($C_{1-4}$alkyl)ureido are N',N'-dimethyl-N-ethylureido and N'-methyl-N'-propyl-N-butylureido; examples of N—($C_{1-4}$alkyl)sulphamoyl are N-methylsulphamoyl and N-isopropylsulphamoyl; examples of N,N-di-($C_{1-4}$alkyl)sulphamoyl are N-methyl-N-ethylsulphamoyl and N,N-dipropylsulphamoyl; and examples of $C_{1-4}$alkylsulphonylamino are mesylamino, ethylsulphonylamino and propylsulphonylamino.

A suitable pharmaceutically acceptable salt of a pyrimidine derivative of the invention is, for example, an acid-addition salt of a pyrimidine derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a pyrimidine derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable cation, for example a salt with methylamine, dimethylamine, trimethylamine, piperidine, morpholine or tris-(2-hydroxyethyl)amine.

The compounds of the formula (I) may be administered in the form of a pro-drug which is broken down in the human or animal body to give a compound of the formula (I). Examples of pro-drugs include in vivo hydrolysable esters of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

Some compounds of the formula (I) may have chiral centres and/or geometric isomeric centres (E- and Z-isomers), and it is to be understood that the invention encompasses all such optical, diastereo-isomers and geometric isomers that possess CDK inhibitory activity.

The invention relates to any and all tautomeric forms of the compounds of the formula (I) that possess CDK inhibitory activity.

It is also to be understood that certain compounds of the formula (I) can exist in solvated as well as unsolvated forms such as, for example, hydrated forms. It is to be understood that the invention encompasses all such solvated forms which possess CDK inhibitory activity.

Particular preferred compounds of the invention comprise a pyrimidine derivative of the formula (I), or pharmaceutically acceptable salt or in vivo hydrolysable ester thereof, wherein $R^1$, $Q_1$, $Q_2$, and G have any of the meanings defined hereinbefore, or any of the following values. Such values may be used where appropriate with any of the definitions, claims or embodiments defined hereinbefore or hereinafter.

Preferably $Q_1$ and $Q_2$ are independently selected from phenyl and pyridyl.

Preferably $Q_1$ is phenyl.

Preferably $Q_2$ is phenyl or pyridyl.

Preferably $Q_1$ is phenyl and $Q_2$ is selected from phenyl or pyridyl.

More preferably $Q_1$ and $Q_2$ are phenyl.

Preferably one of $Q_1$ and $Q_2$ or both $Q_1$ and $Q_2$ is substituted on a ring carbon by one group selected from sulphamoyl, N—($C_{1-4}$alkyl)sulphamoyl, N,N-di-($C_{1-4}$alkly) sulphamoyl (optionally substituted by hydroxy), $C_{1-4}$alkylsulphonyl or a substituent of formula (Ia) wherein:

Y is —S(O)$_2$NH— or —S(O)$_2$—;

Z is $R^a$O—, $R^b R^c$N— or a heterocyclic group; wherein heterocyclic group are optionally substituted on a ring carbon by one or more groups selected from $R^h$;

$R^a$, $R^b$ and $R^c$ are independently selected from hydrogen, $C_{1-4}$alkyl and phenyl;

n is 0;

m is 2 or in addition m may be 0 when Z is a heterocyclic group.

More preferably one of $Q_1$ and $Q_2$ or both of $Q_1$ and $Q_2$ is substituted on a ring carbon by one group selected from sulphamoyl, N—($C_{1-4}$alkyl)sulphamoyl, N,N-di-($C_{1-4}$alkyl) sulphamoyl (optionally substituted by hydroxy), $C_{1-4}$alkylsulphonyl or a substituent of formula (Ia) wherein:

Y is —S(O)$_2$NH— or —S(O)$_2$—;

Z is $R^a$O—, $R^b R^c$N—, thiazolyl, isoxazolyl, thiadiazolyl, pyridyl or morpholino; wherein thiazolyl, isoxazolyl, thiadiazolyl, pyridyl or morpholino are optionally substituted on a ring carbon by one or more methyl;

$R^a$, $R^b$ and $R^c$ are independently selected from hydrogen, $C_{1-4}$alkyl and phenyl;

n is 0;

m is 2 or in addition m may be 0 when Z is thiazolyl, isoxazolyl, thiadiazolyl or pyridyl.

Particularly one of $Q_1$ and $Q_2$ or both of $Q_1$ and $Q_2$ is substituted on a ring carbon by one group selected from sulphamoyl, mesyl, N-(2-diethylaminoethyl)sulphamoyl, 2-(N-methyl-N-phenylamino)ethylsulphonyl, 2-morpholinoethylsulphonyl, N-(5-methylthiadiazol-2-yl)sulphamoyl, N,N-di-(2-hydroxyethyl)sulphamoyl, N-(thiazol-2-yl)sulphamoyl, N-(3,4-dimethylisoxazol-5-yl)sulphamoyl, N-(pyrid-2-yl)sulphamoyl and N-methylsulphamoyl.

More particularly one of $Q_1$ and $Q_2$ or both of $Q_1$ and $Q_2$ is substituted on a ring carbon by one group selected from sulphamoyl and N-methylsulphamoyl.

Preferably it is $Q_1$ that is substituted by one group selected from sulphamoyl, N—($C_{1-4}$alkyl)sulphamoyl (optionally substituted by halo or hydroxy), N,N-di-($C_{1-4}$alkyl)sulphamoyl (optionally substituted by halo or hydroxy), $C_{1-4}$alkylsulphonyl (optionally substituted by halo or hydroxy) or a substituent of the formula (Ia) or (Ia'); and $Q_2$ is optionally additionally substituted by one group selected from sulphamoyl.

More preferably it is $Q_1$ that is substituted in the para- or meta-position relative to the —NH— by sulphamoyl, N—($C_{1-4}$alkyl)sulphamoyl (optionally substituted by halo or hydroxy), N,N-di-($C_{1-4}$alkyl)sulphamoyl (optionally substituted by halo or hydroxy), $C_{1-4}$alkylsulphonyl (optionally substituted by halo or hydroxy) or a substituent of the formula (Ia) or (Ia'); and $Q_2$ is optionally additionally substituted by one group selected from sulphamoyl para to G.

Particularly it is $Q_1$ that is substituted in the para-position relative to the —NH— by sulphamoyl, N—($C_{1-4}$alkyl) sulphamoyl (optionally substituted by halo or hydroxy), N,N-di-($C_{1-4}$alkyl)sulphamoyl (optionally substituted by halo or hydroxy), $C_{1-4}$alkylsulphonyl (optionally substituted by halo or hydroxy) or a substituent of the formula (Ia) or (Ia'); and $Q_2$ is optionally additionally substituted by one group selected from sulphamoyl para to G.

In one aspect of the invention preferably G is —O—.

In another aspect of the invention preferably G is —S—.

In a further aspect of the invention preferably G is —NR$^2$—.

In one aspect of the invention preferably G is —O— or —NR$^2$—.

In one aspect of the invention when G is —NR$^2$—, preferably R$^2$ is hydrogen.

In another aspect of the invention when G is —NR$^2$—, preferably R$^2$ is not hydrogen Preferably G is —O— or —NR$^2$— wherein R$^2$ is selected from hydrogen, $C_{1-6}$alkyl and $C_{3-6}$alkenyl; wherein said $C_{1-6}$alkyl and $C_{3-6}$alkenyl are optionally substituted by one or more halo, cyano or phenyl.

More preferably G is —O— or —NR$^2$— wherein R$^2$ is selected from hydrogen, $C_{1-6}$alkyl and $C_{3-6}$alkenyl; wherein said $C_{1-6}$alkyl and $C_{3-6}$alkenyl are optionally substituted by one or more halo or phenyl.

Particularly G is —O—, —NH—, -(4,4,4-trifluorobutyl)N—, -(3-bromo-2-propenyl)N— or -(3-phenyl-2-propenyl) N—.

More particularly G is —O— or —NH—.

Preferably R$^1$ is hydrogen or halo.

More preferably R$^1$ is hydrogen, chloro or bromo.

Preferably $Q_1$ is optionally substituted by one $C_{1-4}$alkoxy substituent and is substituted by one group selected from sulphamoyl, N—($C_{1-4}$alkyl)sulphamoyl (optionally substituted by halo or hydroxy), N,N-di-($C_{1-4}$alkyl)sulphamoyl (optionally substituted by halo or hydroxy), $C_{1-4}$alkylsulphonyl (optionally substituted by halo or hydroxy) or a substituent of the formula (Ia) or (Ia').

More preferably $Q_1$ is substituted by one group selected from sulphamoyl, N—($C_{1-4}$alkyl)sulphamoyl or N,N-di-($C_{1-4}$alkyl)sulphamoyl.

Preferably $Q_2$ is unsubstituted or substituted by one or two groups selected from halo, cyano, $C_{1-4}$alkyl, $C_{1-4}$alkoxy and a heterocyclic group.

More preferably $Q_2$ is optionally substituted on a ring carbon by one to two substituents independently selected from halo, cyano, methyl, methoxy and morpholino.

Particularly $Q_2$ is optionally substituted on a ring carbon by one to two substituents independently selected from cyano and methoxy.

Preferably $Q_2$ is phenyl, 2-morpholinophenyl, 2-cyanophenyl, 4-bromophenyl, 2-fluoro-5-methylphenyl, 4-methoxyphenyl or 4-sulphamoylphenyl.

More preferably $Q_2$ is phenyl, 2-cyanophenyl, 4-methoxyphenyl or 4-sulphamoylphenyl.

Therefore, in a preferred aspect of the invention there is provided a pyrimidine derivative of the formula (I) as depicted above, wherein:

$Q_1$ and $Q_2$ are independently selected from phenyl and pyridyl; and one of $Q_1$ and $Q_2$ or both $Q_1$ and $Q_2$ is substituted on a ring carbon by one group selected from sulphamoyl, N—($C_{1-4}$alkyl)sulphamoyl, N,N-di-($C_{1-4}$alkyl) sulphamoyl (optionally substituted by hydroxy), $C_{1-4}$alkylsulphonyl or a substituent of formula (Ia) wherein:

Y is —S(O)$_2$NH— or —S(O)$_2$—;

Z is $R^a$O—, $R^b R^c$N— or a heterocyclic group; wherein heterocyclic group are optionally substituted on a ring carbon by one or more groups selected from $R^h$;

$R^a$, $R^b$ and $R^c$ are independently selected from hydrogen, $C_{1-4}$alkyl and phenyl;

n is 0;

m is 2 or in addition m may be 0 when Z is a heterocyclic group;

G is —O— or —NR$^2$— wherein R$^2$ is selected from hydrogen, $C_{1-6}$alkyl and $C_{3-6}$alkenyl;

wherein said $C_{1-6}$alkyl and $C_{3-6}$alkenyl are optionally substituted by one or more halo or phenyl;

$R^1$ is hydrogen or halo;

or pharmaceutically acceptable salt or in vivo hydrolysable ester thereof.

Therefore, in a more preferred aspect of the invention there is provided a pyrimidine derivative of the formula (I) as depicted above, wherein:

$Q_1$ is phenyl optionally substituted by one $C_{1-4}$alkoxy substituent and $Q_2$ is phenyl optionally substituted by one or more halo, cyano, methyl, methoxy and morpholino; and $Q_1$ is substituted in the para-position relative to the —NH— by one group selected from sulphamoyl, mesyl, N-(2-diethylaminoethyl)sulphamoyl, 2-(N-methyl-N-phenylamino)ethylsulphonyl, 2-morpholinoethylsulphonyl, N-(5-methylthiadiazol-2-yl)sulphamoyl, N,N-di-(2-hydroxyethyl)sulphamoyl, N-(thiazol-2-yl)sulphamoyl, N-(3,4-dimethylisoxazol-5-yl)sulphamoyl, N-(pyrid-2-yl)sulphamoyl and N-methylsulphamoyl; and $Q_2$ is optionally substituted by one group selected from sulphamoyl;

G is —O—, —NH—, -(4,4,4-trifluorobutyl)N—, -(3-bromo-2-propenyl)N— or -(3-phenyl-2-propenyl)N—;

$R^1$ is hydrogen, chloro or bromo or pharmaceutically acceptable salt or in vivo hydrolysable ester thereof.

In one aspect of the invention preferred compounds of the invention are those of Examples 1, 20, 21, 29 or 31 or pharmaceutically acceptable salt or in vivo hydrolysable ester thereof.

In a further aspect of the invention preferred compounds of the invention include any one of the Examples or pharmaceutically acceptable salt or in vivo hydrolysable ester thereof.

Preferred aspects of the invention are those which relate to the compound or a pharmaceutically acceptable salt thereof.

A pyrimidine derivative of the formula (I), or a pharmaceutically acceptable salt or an in vivo hydrolysable ester thereof, may be prepared by any process known to be applicable to the preparation of chemically-related compounds. Such processes, when used to prepare a pyrimidine derivative of the formula (I), or a pharmaceutically acceptable salt or an in vivo hydrolysable ester thereof, are provided as a further feature of the invention and are illustrated by the following representative examples in which, unless otherwise stated $R^1$, $Q_1$, $Q_2$ and G have any of the meanings defined hereinbefore for a pyrimidine derivative of the formula (I) and unless another substituent is drawn on ring $Q_1$ or $Q_2$ the ring may bear any of the substituents described hereinbefore (optionally protected as necessary). Where a substituent is drawn on ring $Q_1$, this includes (unless stated otherwise) the possibilities of the substituent being on ring $Q_2$ in addition to, or instead of the substituent being on ring $Q_1$. Necessary starting materials may be obtained by standard procedures of organic chemistry (see for example, Advanced Organic Chemistry (Wiley-Interscience), Jerry March—also useful for general guidance on reaction conditions and reagents). The preparation of such starting materials is described within the accompanying non-limiting processes and Examples. Alternatively necessary starting materials are obtainable by analogous procedures to those illustrated which are within the ordinary skill of an organic chemist.

Thus, as a further feature of the invention there are provided the following processes which comprises of:

a) for compounds of formula (I) where G is —$NR^2$—; reacting a pyrimidine of formula (II):

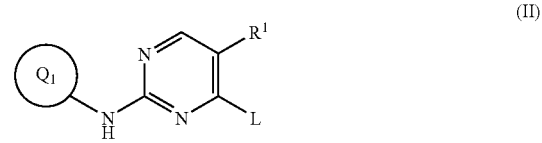

wherein L is a displaceable group as defined below, with a compound of formula (III):

where G is —$NR^2$—;

b) reaction of a pyrimidine of formula (IV):

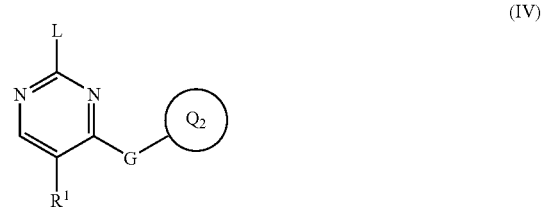

wherein L is a displaceable group as defined below, with a compound of formula (V):

c) for compounds of formula (I) wherein the sidechain is of formula (Ia) and Y is —$S(O)_2NH$—; by reaction of a compound of formula (VI):

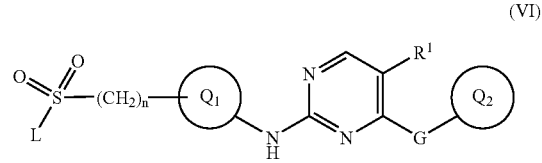

where L is a displaceable group; with an amine of formula (VII:

d) for compounds of formula (I) wherein the sidechain is of formula (Ia) and Y is —NHS(O)$_2$— by reaction of an amine of formula (VIII):

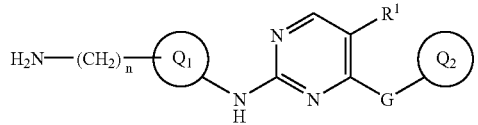

with a compound of formula (IX):

Z-(CH$_2$)$_m$—SO$_2$L     (IX)

where L is a displaceable group;

e) for compounds of formula (I) wherein the sidechain is of formula (Ia'); by reaction of a compound of formula (VI) with an amine of formula (X):

and thereafter if necessary:
i) converting a compound of the formula (I) into another compound of the formula (I);
ii) removing any protecting groups;
iii) forming a pharmaceutically acceptable salt or in vivo hydrolysable ester.

The skilled reader will also appreciate that process c) can also be use to make compounds of formula (I) wherein one of Q$_1$ and Q$_2$ or both Q$_1$ and Q$_2$ is substituted on a ring carbon by one group selected from sulphamoyl, N—(C$_{1-4}$alkyl)sulphamoyl (optionally substituted by halo or hydroxy) or N,N-di-(C$_{1-4}$alkyl)sulphamoyl (optionally substituted by halo or hydroxy).

L is a displaceable group, suitable values for L are for example, a halo, sulphonyloxy or sulphur group, for example a chloro, bromo, methanesulphonyloxy, toluene-4-sulphonyloxy, mesyl, methylthio and methylsulphinyl.

Specific reaction conditions for the above reactions are as follows:

Process a)
Pyrimidines of formula (II) and compounds of formula (III) may be reacted together:
i) optionally in the presence of a suitable acid, for example an inorganic acid such as hydrochloric acid or sulphuric acid, or an organic acid such as acetic acid or formic acid. The reaction is preferably carried out in a suitable inert solvent or diluent, for example dichloromethane (DCM), acetonitrile, butanol, tetramethylene sulphone, tetrahydrofuran, 1,2 dimethoxyethane, N,N-dimethylformamide, N,N-dimethylacetamide or N-methylpyrrolidin-2-one, and at a temperature in the range, for example, 0° to 150° C., conveniently at or near reflux temperature; or
ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) may be prepared according to the following scheme:

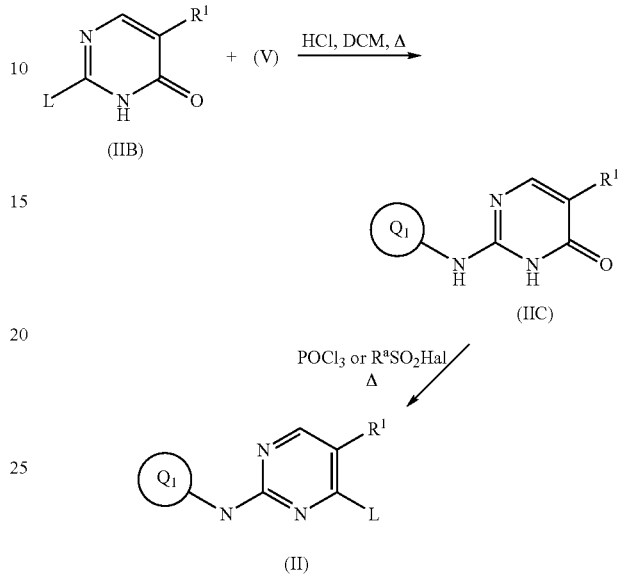

wherein L is a displaceable group as defined above.

Compounds of formula (IIB) and (III) are commercially available or are prepared by processes known in the art.

Process b)
Pyrimidines of formula (IV) and anilines of formula (V) may be reacted together, i) in the presence of a suitable solvent for example a ketone such as acetone or an alcohol such as ethanol or butanol or an aromatic hydrocarbon such as toluene or N-methylpyrrolidine, optionally in the presence of a suitable acid such as those defined above (or a suitable Lewis acid) and at a temperature in the range of 0° C. to reflux, preferably reflux; or ii) under standard Buchwald conditions as described above.

Pyrimidines of formula (IV) are prepared according to the following scheme:

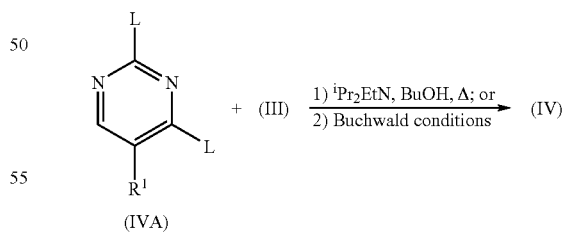

wherein L is a displaceable group as defined above.

The anilines of formula (V) are commercially available or are prepared by processes known in the art.

Pyrimidines of the formula (IVA) are commercially available or may be prepared by, for example, reacting a compound of formula (IVA) in which L is —OH (i.e. a uracil), with POCl$_3$ to give a compound of formula (IVA) in which L is —Cl.

Process c)

Compounds of formula (VI) and amines of formula (VII) may be coupled together in the presence of a base, for example a tertiary amine such as triethylamine and in the presence of a catalyst for example dimethylaminopyridine. Suitable solvents for the reaction include nitrites such as acetonitrile and amides such as dimethylformamide. The reaction is conveniently performed at a temperature in the range of from 0 to 120° C.

Compounds of formula (VI) (for example when L is chlorine) may be prepared according to the following scheme:

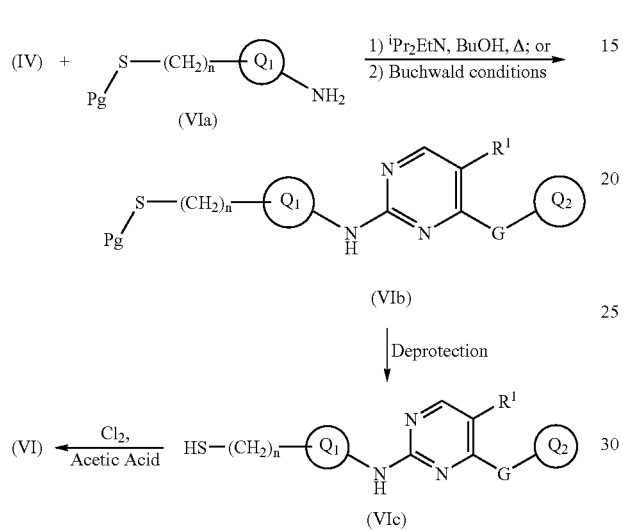

wherein Pg is a suitable sulphur protecting group such as those described below.

Amines of formula (VII) and amines of formula (VIa) are commercially available or are prepared by processes known in the art.

Process d)

Compounds of formula (IX) and amines of formula (VIII) may be coupled together under the conditions described in process c) above.

Amines of formula (VIII) may be prepared according to the following scheme:

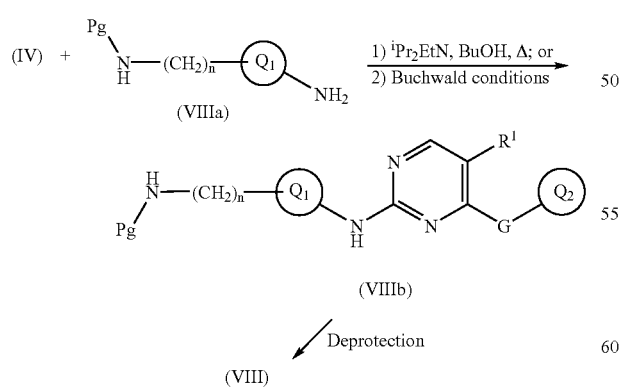

wherein Pg is a suitable amino protecting group such as those described hereinbelow.

Compounds of formula (IX) are commercially available or are prepared by processes known in the art.

Process e)

Compounds of formula (VI) and amines of formula (X) may be coupled together under the conditions described in process c) above.

Amines of formula (X) are commercially available or are prepared by processes known in the art.

Examples of conversions of a compound of formula (I) into another compound of formula (I) are:

i) where G is —NR²—; conversion of R² as hydrogen into other R² for example:

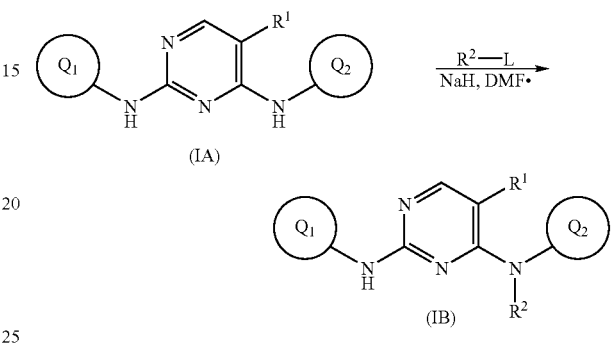

wherein L is a displaceable group;

ii) where G is —NR²—; conversion of R² as a substituted side chain into another substituted side chain, for example:

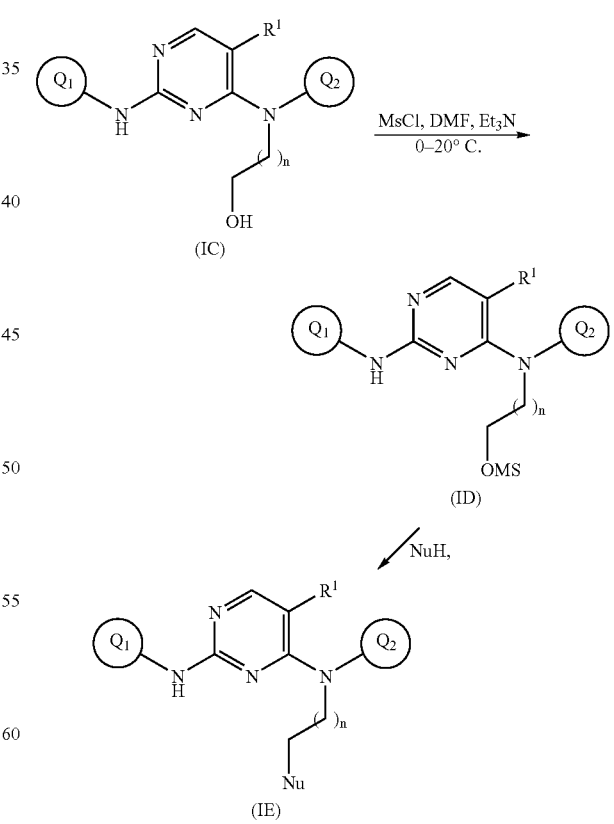

wherein Ms is methanesulphonyl, and Nu is a nucleophile that introduces a substituent that is an optional substituent for R² as defined in formula (I) (NB the hydroxyl moiety does not necessarily have to be on the terminal carbon as depicted above);
iii) conversion of one side chain of formula (Ia) into another side chain of formula (Ia)
iv) conversion of one value of R¹ into another value of R¹, using standard techniques, for example, conversion of R¹ as hydroxy into $C_{1-4}$alkoxy.

The skilled reader will appreciate that the formation of the side chain (Ia) or (Ia') described in Processes c), d) and e) above and of the sidechain R² in i) and ii) above may also be performed on intermediates.

A preferred process of the invention is Process b).

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halo group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a thio group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an acetyl or benzoyl group may be removed, for example, by cleavage with sodium and ammonia.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Many of the intermediates defined herein are novel, for example, those of the formula II and IV and these are provided as a further feature of the invention.

Assays

As stated hereinbefore the pyrimidine derivative defined in the present invention possesses anti-cell-proliferation activity such as anti-cancer activity which is believed to arise from the CDK inhibitory activity of the compound. These properties may be assessed, for example, using the procedure set out below:

CDK4 Inhibition Assay

The following abbreviations have been used:
HEPES is N-(2-Hydroxyethyl)piperaiine-N'-(2-ethanesulfonic acid)
DTT is Dithiothretiol
PMSF is Phenylmethylsulfonyl fluoride The compounds were tested in an in vitro kinase assay in 96 well format using Scintillation Proximity Assay (SPA— obtained from Amersham) for measuring incorporation of [γ-33-P]-Adenosine Triphosphate into a test substrate (GST-Retinoblastoma). In each well was placed the compound to be tested (diluted in DMSO and water to correct concentrations) and in control wells either p16 as an inhibitor control or DMSO as a positive control.

Approximately 0.5 μl of CDK4/Cyclin D1 partially-purified enzyme (amount dependent on enzyme activity) diluted in 25 μl incubation buffer was added to each well then 20 μl of GST-Rb/ATP/ATP33 mixture (containing 0.5 μg GST-Rb and 0.2 μM ATP and 0.14 μCi [γ-33-P]-Adenosine Triphosphate), and the resulting mixture shaken gently, then incubated at room temperature for 60 minutes.

To each well was then added 150 μL stop solution containing (0.8 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124×g., for 5 minutes. The plates were read on a Topcount for 30 seconds per well.

The incubation buffer used to dilute the enzyme and substrate mixes contained 50 mM HEPES pH 7.5, 10 mM $MnCl_2$, 1 mM DTT, 100 μM Sodium vanadate, 100 μM NaF, 10 mM Sodium Glycerophosphate, BSA (1 mg/ml final).

As a control, another known inhibitor of CDK4 may be used in place of p16.

Test Substrate

In this assay only part of the retinoblastoma (Science 1987 Mar. 13;235(4794):1394–1399; Lee W. H., Bookstein R., Hong F., Young L. J., Shew J. Y., Lee E. Y.) was used, fused to a GST tag. PCR of retinoblastoma amino acids 379–928 (obtained from retinoblastoma plasmid ATCC pLRbRNL) was performed, and the sequence cloned into pGEX 2T fusion vector (Smith D. B. and Johnson, K. S. Gene 67, 31 (1988); which contained a tac promoter for inducible expression, internal lac $I^q$ gene for use in any E. Coli host, and a coding region for thrombin cleavage—obtained from Pharmacia Biotech) which was used to amplify amino acids 792–928. This sequence was again cloned into pGEX 2T.

The retinoblastoma 792–928 sequence so obtained was expressed in E. Coli (BL21 (DE3) pLysS cells) using standard inducible expression techniques, and purified as follows.

E. coli paste was resuspended in 10 ml/g of NETN buffer (50 mM Tris pH 7.5, 120 mM NaCl, 1 mM EDTA, 0.5% v/v NP-40, 1 mM PMSF, 1 ug/ml leupeptin, 1 ug/ml aprotinin and 1 ug/ml pepstatin) and sonicated for 2×45 seconds per 100 ml homogenate. After centrfugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM MgCl2, 1 mM DTT, 1 mM PMSF, 1 ug/ml leupeptin, 1 ug/ml aprotinin and 1 ug/ml pepstatin) the protein was eluted with 50 mM reduced glutathione in kinase buffer. Fractions containing GST-Rb(792–927) were pooled and dialysed overnight against kinase buffer. The final product was analysed by Sodium Dodeca Sulfate (SDS) PAGE (Polyacrylamide gel) using 8–16% Tris-Glycine gels (Novex, San Diego, USA).

CDK4 and Cyclin D1

CDK4 and Cyclin D1 were cloned from RNA from MCF-7 cell line (obtained from ATCC number:HTB22, breast adenocarcinoma line) as follows. The RNA was prepared from MCF-7 cells, then reverse transcribed using oligo dT primers. PCR was used to amplify the complete coding sequence of each gene [CDK4 amino acids 1–303; Ref. Cell Oct. 16, 1992; 71(2): 323–334; Matsushime H., Ewen M. E., Stron D. K., Kato J. Y., Hanks S. K., Roussel M. F., Sherr C. J. and Cyclin D1 amino acids 1–296; Ref. Cold Spring Harb. Symp. Quant. Biol., 1991; 56:93–97; Arnold A., Motokura T., Bloom T., Kronenburg, Ruderman J., Juppner H., Kim H. G.].

After sequencing the PCR products were cloned using standard techniques into the insect expression vector pVL1393 (obtained from Invitrogen 1995 catalogue number: V1392–20). The PCR products were then dually expressed [using a standard virus Baculogold co-infection technique] into the insect SF21 cell system (*Spodoptera Frugiperda* cells derived from ovarian tissue of the Fall Army Worm—Commercially available).

The following Example provides details of the production of Cyclin D1/CDK4 in SF21 cells (in TC100+10% FBS (TCS)+0.2% Pluronic) having dual infection MOI 3 for each virus of Cyclin D1 & CDK4.

Example production of Cyclin D1/CDK4

SF21 cells grown in a roller bottle culture to $2.33×10^6$ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

10×500 ml were infected with JS303 Cyclin D1 virus titre—9×10E7 pfu/ml. JS304 CDK4 virus titre—1×10E8 pfu/ml.

$$Cyclin\,D1\quad \frac{1.86\times 10E6\times 500\times 3}{0.9\times 10^8} = \begin{array}{l}31\text{ ml of virus for}\\ \text{each 500 ml. bottle.}\end{array}$$

$$CDK4\quad \frac{1.86\times 10E6\times 500\times 3}{1\times 10^8} = \begin{array}{l}28\text{ ml of virus for}\\ \text{each 500 ml. bottle.}\end{array}$$

The viruses were mixed together before addition to the cultures, and the cultures returned to the roller rig 28° C.

After 3 days (72 hrs.) post infection the 5 Litres of culture was harvested. The total cell count at harvest was 1.58×10E6 cells/ml.(99% viable). The cells were spun out at 2500 rpm, 30 mins., 4° C. in Heraeus Omnifuge 2.0 RS in 250 ml lots. The supernatant was discarded. 20 pellets of ~4×10E8 cells/pellet were snap frozen in $LN_2$ and stored at −80° C. in CCRF cold room. The SF21 cells were then hypotonically lysed by resuspending in lysis buffer (50 mM HEPES pH 7.5, 10 mM magnesium chloride, 1 mM DTT, 10 mM glycerophosphate, 0.1 mM PMSF, 0.1 mM sodium fluoride, O. 1 mM sodium orthovanadate, 5 ug/ml aprotinin, 5 ug/ml leupeptin and 20% w/v sucrose), and adding ice cold deionised water. After centrifugation, the supernatant was loaded onto a Poros HQ/M 1.41100 anion exchange column (PE Biosystems, Hertford, UK). CDK4 and Cyclin D1 were coeluted with 375 mM NaCl in lysis buffer, and their presence checked by western blot, using suitable anti-CDK4 and anti-Cyclin D1 antibodies (obtained from Santa Cruz Biotechnology, California, US).

p16 Control (Nature 366,:704–707; 1993; Serrano M, Hannon G J, Beach D)

p16 (the natural inhibitor of CDK4/Cyclin D1) was amplified from HeLa cDNA (Hela cells obtained from ATCC CCL2, human epitheloid carcinoma from cervix; Cancer Res. 12: 264, 1952), cloned into pTB 375 NBSE which had a 5' His tag, and transformed using standard techniques into BL21 (DE3) pLysS cells (obtained from Promega; Ref. Studier F. W. and Moffat B. A., J. Mol. Biol., 189, 113, 1986). A 1 litre culture was grown to the appropriate OD then induced with IPTG to express p16 overnight. The cells were then lysed by sonication in 50 mM sodium phosphate, 0.5M sodium chloride, PMSF, 0.5 µg/ml leupeptin and 0.5 µg/ml aprotinin. The mixture was spun down, the supernatant added to nickel chelate beads and mixed for 1½ hours. The beads were washed in sodium phosphate, NaCl pH 6.0 and p16 product eluted in sodium phosphate, NaCl pH 7.4 with 200 mM imidazole.

The pTB NBSE was constructed from pTB 375 NBPE as follows:

pTB375

The background vector used for generation of pTB 375 was pZEN0042 (see UK patent 2253852) and contained the tetA/tetR inducble tetracycline resistance sequence from plasmid RP4 and the cer stability sequence from plasmid pKS492 in a pAT153 derived background. pTB375 was generated by the addition of an expression cassette consisting of the T7 gene 10 promoter, multiple cloning site and T7 gene 10 termination sequence. In addition, a terminator sequence designed to reduce transcriptional readthrough from the background vector was included upstream of the expression cassette.

pTB 375 NBPE

The unique EcoRI restriction site present in pTB 375 was removed. A new multiple cloning site containing the recognition sequences for the restriction enzymes NdeI, BamHI, PstI and EcoRI was introduced into pTB 375 between the NdeI and BamHI sites destroying the original BamHI site present in pTB 375.

pTB 375 NBSE

A new multiple cloning site containing the recognition sequences for the restriction enzymes NdeI, BamHI, SmaI and EcoRI was introduced into pTB 375 NBPE between the NdeI and EcoRI sites. The oligonucleotide containing these restriction sites also contained 6 histidine codons located between the NdeI and BamHI sites in the same reading frame as the inititiator codon (ATG) present within the NdeI site.

By analogy to the above, assays designed to assess inhibition of CDK2 and CDK6 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

If using CDK2 with Cyclin E partial co-purification may be achieved as follows:

Sf21 cells are resuspended in lysis buffer (50 mM Tris pH 8.2, 10 mM $MgCl_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homgeniser. After centrifugation, the supernatant is loaded onto a Poros HQ/M 1.4/100 anion exchange column (PE Biosystems, Hertford, UK). CDK2 and Cyclin E are coeluted at the beginning of a 0–1M NaCl gradient (run in lysis buffer minus protease inhibitors) over 20 column volumes. Co-elution is checked by western blot using both anti-CDK2 and anti-Cyclin E antibodies (Santa Cruz Biotechnology, California, US).

Although the pharmacological properties of the compounds of the formula (I) vary with structural change, in general activity possessed by compounds of the formula (I) in the above assays may be demonstrated at $IC_{50}$ concentrations or doses in the range 250 µM to 1 nM.

When tested in the above in vitro assay the CDK2 inhibitory activity of Example 23 was measured as $IC_{50}=0.347$ µM.

The in vivo activity of the compounds of the present invention may be assessed by standard techniques, for example by measuring inhibition of cell growth and assessing cytotoxicity.

Inhibition of cell growth may be measured by staining cells with Sulforhodamine B (SRB), a fluorescent dye that stains proteins and therefore gives an estimation of amount of protein (i.e. cells) in a well (see Boyd, M. R. (1989) Status of the NCI preclinical antitumour drug discovery screen. Prin. Prac Oncol 10:1–12). Thus, the following details are provided of measuring inhibition of cell growth:

Cells were plated in appropriate medium in a volume of 100 µl in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DMSO (v/v). A control plate was assayed to give a value for cells before dosing. Cells were incubated at 37° C., (5% CO2) for three days.

At the end of three days TCA was added to the plates to a final concentration of 16% (v/v). Plates were then incubated at 4° C. for 1 hour, the supernatant removed and the plates washed in tap water. After drying, 100 µl SRB dye (0.4% SRB in 1% acetic acid) was added for 30 minutes at 37° C. Excess SRB was removed and the plates washed in 1% acetic acid. The SRB bound to protein was solubilised in 10 mM Tris pH 7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical $IC_{50}$ values for compounds of the invention when tested in the SRB assay are in the range 1 mM to 1 nM.

According to a further aspect of the invention there is provided a pharmaceutical composition which comprises a pyrimidine derivative of the formula (I), or a pharmaceutically acceptable salt or in vivo hydrolysable ester thereof, as defined hereinbefore in association with a pharmaceutically acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The pyrimidine will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a pyrimidine derivative of the formula (I), or a pharmaceutically acceptable salt or in vivo hydrolysable ester thereof, as defined hereinbefore for use in a method of prophylactic or therapeutic treatment of a warm-blooded animal, such as man.

We have found that the pyrimidine derivatives defined in the present invention, or a pharmaceutically acceptable salt or in vivo hydrolysable ester thereof, are effective cell cycle inhibitors (anti-cell proliferation agents), which property (without being bound by theory) is believed to arise from their CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds may be used to produce an anti-proliferative effect mediated alone or in part by the inhibition of CDKs. Such a pyrimidine derivative of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a pyrimidine derivative of the invention will possess anti-cancer activity against these cancers. It is in addition expected that a pyrimidine derivative of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDK, especially those tumours which are significantly dependent on CDK for their growth and spread, including for example, certain tumours of the colon, breast, prostate, lung, vulva and skin.

It is further expected that a pyrimidine derivative of the present invention will possess activity against other cell-proliferation diseases in a wide range of other disease states including leukemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a pyrimidine derivative of the formula (I), or a pharmaceutically acceptable salt or in vivo hydrolysable ester thereof, as defined hereinbefore for use as a medicament; and the use of a pyrimidine derivative of the formula (I), or a pharmaceutically acceptable salt or in vivo hydrolysable ester thereof, as defined hereinbefore in the manufacture of a medicament for use in the production of an anti-cancer, cell cycle inhibitory (anti-cell-proliferation) effect in a warm-blooded animal such as man. Particularly, a cell cycle inhibitory effect is produced at the S or G1-S phase by inhibition of CDK2, CDK4 and/or CDK6, especially CDK2.

According to a further feature of this aspect of the invention there is provided a method for producing an anti-cancer, cell cycle inhibitory (anti-cell-proliferation) effect in a warm-blooded animal, such as man, in need of such treatment which comprises administering to said animal an effective amount of a pyrimidine derivative as defined immediately above. Particularly, an inhibitory effect is produced at the S or G1-S phase by inhibition of CDK2, CDK4 and/or CDK6, especially CDK2.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The CDK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;
(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan). According to this aspect of the invention there is provided a pharmaceutical product comprising a pyrimidine derivative of the formula (I) as defined hereinbefore, or a pharmaceutically acceptable salt or in vivo hydrolysable ester thereof, and an additional anti-tumour substance as defined hereinbefore for the conjoint treatment of cancer. An anti-emetic may also be usefully administered, for example when using such conjoint treatment as described above.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other, pharmaceutical composition, process, method, use and medicament manufacture features, the alternative and preferred embodiments of the compounds of the invention described herein also apply.

The invention will now be illustrated in the following non-limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) operations were carried out at ambient temperature, typically in the range 18–25° C. and in air unless stated, or unless the skilled person would otherwise operate under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points where given were determined using a Mettler SP62 automatic melting point apparatus, an oil-bath apparatus or a Koffler hot plate apparatus.

(vi) the structures of the end-products of the formula (I) were generally confirmed by nuclear (generally proton) magnetic resonance (NMR) and mass spectral techniques; proton magnetic resonance chemical shift values were measured in deuterated DMSO-$d_6$ (unless otherwise stated) on the delta scale (ppm downfield from tetramethylsilane) using a Varian Gemini 2000 spectrometer operating at a field strength of 300 MHz unless otherwise stated; and peak multiplicities are shown as follows: s, singlet; d, doublet; t, triplet; m, multiplet; br, broad; mass spectrometry (MS) was performed by electrospray on a VG platform;

(vii) intermediates were not generally fully characterised and purity was assessed by thin layer chromatography (TLC), high performance liquid chromatography (HPLC), infra-red (IR), MS or NMR analysis;

(viii) the following abbreviations may be used hereinbefore or hereinafter:

| | |
|---|---|
| DMF | N,N-dimethylformamide; |
| NMP | N-methylpyrrolidin-2-one; |
| DMSO | dimethylsulphoxide; |
| Rt | retention time; |

(ix) System A:

| | |
|---|---|
| Column | 4.6 mm × 10 cm Hichrom RPB 5A |
| Solvent | A = 95% water, 5% acetonitrile + 0.1% Formic acid |
| | B = 95% acetonitrile, 5% water + 0.1% Formic acid |
| Run time | 10 minutes with a 9.5 minute gradient from 5–95% B |
| Wavelength | 254 nm bandwidth 10 nm |
| Mass detector | Platform LC |

EXAMPLE 1

2-(4-Sulphamoylanilino)-4-(2-cyanoanilino)pyrimidine

2-Chloro-4-(2-cyanoanilino)pyrimidine (250 mg, 1.09 mmol) was dissolved in n-butanol (3 ml) and sulphanilamide (150 mg, 0.87 mmol) was added. The resulting suspension was treated with methanol until all the solid dissolved. The reaction mixture was heated at 95° C. for 12 hours and allowed to cool to ambient temperature. The reaction mixture was then basified to pH 9–10 using methanolic ammonia and evaporated onto silica (5 ml). The residue was purified by column chromatography eluting with 0–15% 2.0M methanolic ammonia solution in dichloromethane to afford a solid product (256 mg). NMR (303.1K): 6.58 (d, 1H), 7.24 (br s, 2H), 7.56 (m, 5H), 7.69 (d, 1H), 7.82 (t, 1H), 7.95 (d, 1H), 10.88 (br s, 1H), 11.07 (br s, 1H); MS (M+H)$^+$: 367.1.

EXAMPLES 2–11

The following compounds were prepared by an analogous method to that described in Example 1 using the appropriate 4-sulphonyl aniline and 2-chloro-4-anilinopyrimidine intermediates.

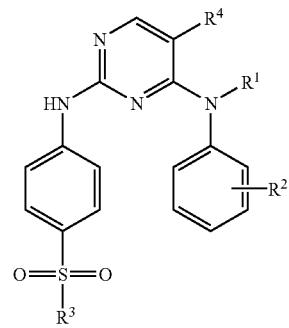

| Ex | R¹ | R² | R³ | R⁴ | NMR, 400 MHz @ 373k | MS (M + H)⁺ |
|---|---|---|---|---|---|---|
| 2 | H | 4-Br | ![HN-CH2CH2-N(Et)2] | H | 0.90 (m, 6H), 2.41 (m, 6H), 2.86 (m, 2H), 6.33 (d, 1H), 6.78 (br s, 1H), 7.47 (d, 2H), 7.64 (m, 4H), 7.89 (d, 2H), 8.09 (d, 1H), 9.24 (br s, 2H) | 519.3, 521.3 |
| 3 | —CH₂CH₂CH₂CF₃ | 4-Br | ![HN-CH2CH2-N(Et)2] | H | 0.99 (m, 6H), 1.95 (m, 2H), 2.39 (m, 2H), 2.50 (m, 6H), 2.92 (m, 2H), 4.07 (m, 2H), 5.97 (d, 1H), 6.80 (br s, 1H), 7.39 (d, 2H), 7.70 (d, 2H), 7.76 (d, 2H), 7.89 (d, 2H), 8.04 (d, 1H), 9.29 (s, 1H) | 629.4, 631.4 |
| 4 | —CH₂CH=CHBr | 4-Br | ![HN-CH2CH2-N(Et)2] | H | 0.84 (t, 6H), 2.37 (m, 6H), 2.78 (m, 2H), 4.45 (d, 1H), 4.58 (d, 1H), 5.85 (d, 1H), 6.40 (m, 2H), 6.66 (br s, 1H), 7.24 (d, 2H), 7.56 (d, 2H), 7.61 (d, 2H), 7.75 (dd, 2H), 7.92 (d, 1H), 9.19 (br s, 1H) | 637.3, 639.3, 641.3 |
| 5 | —CH₂CH=CHPh | 4-Br | ![HN-CH2CH2-N(Et)2] | H | 0.89 (t, 6H), 2.43 (m, 6H), 2.83 (t, 2H), 4.70 (d, 2H), 6.00 (d, 1H), 6.39 (m, 1H), 6.59 (d, 1H), 6.72 (br s, 1H), 7.29 (m, 7H), 7.61 (d, 2H), 7.67 (d, 2H), 7.83 (d, 2H), 8.00 (d, 1H), 9.25 (s, 1H) | 635.4, 637.4 |
| 6 | H | 2-CN | —CH₃ | H | 3.09 (s, 3H), 6.41 (d, 1H), 7.40 (m, 1H), 7.68 (d, 2H), 7.74 (m, 2H), 7.84 (d, 1H), 7.88 (d, 2H), 8.17 (d, 1H), 9.30 (s, 1H), 9.37 (s, 1H) | 366.3 |

Replacing the chemical image placeholders: R³ in examples 2–5 is —CH(CH₃)- type; specifically the structure shown is an HN-CH₂CH₂-N(CH₂CH₃)₂ group (2-(diethylamino)ethylamino).

-continued

| Ex | R¹ | R² | R³ | R⁴ | NMR, 400 MHz @ 373k | MS (M + H)⁺ |
|---|---|---|---|---|---|---|
| 7 | H | 2-F, 5-CH₃ | —NH₂ | H | (303.1K) 2.28 (s, 3H), 6.55 (d, 1H), 7.16 (m, 1H), 7.25 (m, 3H), 7.46 (d, 1H), 7.64 (t, 4H), 8.09 (d, 1H), 10.71 (br s, 1H), 10.98 (br s, 1H) | 374.3 |
| 8 | —CH₂CH₂CH₂CF₃ | 2-F, 5-CH₃ | —CH₃ | H | 1.86 (m, 2H), 2.32 (m, 2H), 2.33 (s, 3H), 3.07 (s, 3H), 3.94 (t, 2H), 5.88 (d, 1H), 7.26 (m, 3H), 7.68 (d, 2H), 7.83 (d, 2H), 8.00 (d, 1H), 9.31 (s, 1H) | 483.4 |
| 9 | —CH₂CH=CHPh | 2-F, 5-CH₃ | —CH₃ | H | 2.32 (s, 3H), 3.06 (s, 3H), 4.65 (d, 2H), 5.97 (d, 1H), 6.37 (m, 1H), 6.61 (d, 1H), 7.28 (m, 8H), 7.66 (d, 2H), 7.87 (d, 2H), 8.02 (d, 1H), 9.35 (s, 1H) | 489.5 |
| 10 | —CH₂CH=CHBr | 2-F, 5-CH₃ | —CH₃ | H | 2.33 (s, 3H), 3.08 (s, 3H), 4.48 (d, 1H), 4.61 (d, 1H), 5.89 (m, 1H), 6.40 (m, 1H), 6.54 (m, 1H), 7.24 (m, 3H), 7.69 (d, 2H), 7.85 (d, 2H), 8.01 (d, 1H), 9.37 (s, 1H) | 491.3, 493.3 |
| 11 | —CH₂CH=CHPh | 2-F, 5-CH₃ | —NH₂ | Cl | 2.28 (s, 3H), 4.71 (d, 2H), 6.39 (m, 1H), 6.52 (d, 1H), 6.75 (br s, 2H), 7.10 (m, 2H), 7.19 (m, 2H), 7.27 (m, 4H), 7.69 (d, 2H), 7.80 (d, 2H), 8.08 (s, 1H), 9.38 (br s, 1H)² | 524.5, 526.4 |
| 12 | H | H | (2,2-dimethyl-4-morpholinobutyl) | Br | NMR (ambient temp) 2.2 (m, 4H), 2.5 (m, 4H), 3.4 (m, 4H), 7.2 (t, 1H), 7.4 (t, 2H), 7.6 (m, 4H), 7.8 (d, 2H), 8.3 (s, 1H), 8.8 (s, 1H), 9.8 (s, 1H) | 518, 520 |

¹Product purified by column chromatography twice followed by recrystallization from methanol.
²Run on a 500 MHz NMR machine.

EXAMPLE 13

2-(4-Sulphamoylanilino)-4-[2-fluoro-5-methyl-N-(4,4,4-trifluorobutyl)anilino]pyrimidine 2-Chloro-4-(N-4,4,4,-trifluorobutyl-2-fluoro-5-methylanilino)pyrimidine (215 mg, 0.62 mmol) was dissolved in n-butanol (2 ml) and sulphanilamide (85 mg, 0.50 mmol) was added. The resulting suspension was treated with methanol until all the solid dissolved. The reaction mixture was heated at 95° C. for 12 hours and allowed to cool to ambient temperature. The solid that had precipitated was collected by filtration, washed with a small volume of methanol and dried in vacuo to yield a white solid (132 mg). NMR (400 MHz@373K): 1.85 (m, 2H), 2.31 (m, 2H), 2.35 (s, 3H), 3.97 (t, 2H), 6.04 (d, 1H), 7.29 (m, 3H) 8.02 (d, 1H), 10.00 (br s, 1H); MS (M+H)⁺: 484.4.

EXAMPLES 14–22

The following compounds were prepared by an analogous method to that described in Example 13 using the appropriate 4-sulphonyl aniline and 2-chloro-4-anilinopyrimidine intermediates.

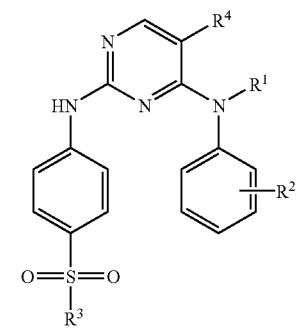

| Ex | R¹ | R² | R³ | R⁴ | NMR, 400 MHz @ 373k | MS (M + H)⁺ |
|----|----|----|----|----|---------------------|-------------|
| 14 | —CH₂CH=CHBr | 2-F, 5-CH₃ | —NH₂ | H | 2.34 (s, 3H), 4.50 (d, 1H), 4.66 (d, 1H), 6.00 (m, 1H), 6.39 (m, 1H), 6.58 (m, 1H), 7.29 (m, 3H), 7.69 (m, 4H), 8.05 (d, 1H), 9.99 (br s, 1H) | 492.3, 494.3 |
| 15 | —CH₂CH=CHPh | 2-F, 5-CH₃ | —NH₂ | H | 2.33 (s, 3H), 4.69 (d, 2H), 6.09 (d, 1H), 6.32 (m, 1H), 6.60 (d, 1H), 7.28 (m, 8H), 7.69 (s, 4H), 8.05 (d, 1H), 10.00 (br s, 1H) | 490.5 |
| 16 | —CH₂CH₂CH₂CF₃ | 2-CN | —NH₂ | H | 1.91 (m, 2H), 2.36 (m, 2H), 4.04 (t, 2H), 6.06 (d, 1H), 7.62 (m, 6H), 7.89 (t, 1H), 7.98 (d, 1H), 8.09 (d, 1H), 9.70 (br s, 1H) | 477.4 |
| 17 | —CH₂CH=CHBr | 2-CN | —NH₂ | H | 4.59 (d, 1H), 4.74 (d, 1H), 6.07 (dd, 1H), 6.48 (m, 1H), 6.65 (m, 1H), 7.65 (m, 6H), 7.90 (m, 1H), 7.99 (d, 1H), 8.12 (d, 1H), 9.79 (br s, 1H) | 485.3, 487.3 |
| 18 | —CH₂CH=CHPh | 2-CN | —NH₂ | H | (500 MHz @ 373K) 4.74 (d, 2H), 6.09 (d, 1H), 6.36 (m, 1H), 6.63 (d, 1H), 7.21 (t, 1H), 7.29 (t, 2H), 7.34 (d, 2H), 7.61 (m, 6H), 7.85 (t, 1H), 7.92 (d, 1H), 8.10 (d, 1H), 9.51 (br s, 1H) | 483.4 |
| 19 | H | H | (2-pyridylamino group) | Br | Rt = 2.46¹ | 498 |
| 20 | H | H | NHCH₃ | Br | Rt = 2.56¹ | 435 |
| 21 | H | H | NH₂ | Br | Rt = 2.40¹ | 421 |
| 22 | H | H | (—(CH₂)₃N(Me)Ph group) | Br | (ambient temperature) 2.7 (s, 3H), 3.38 (m, 2H), 3.6 (m, 2H), 6.55 (d, 2H), 6.6 (t, 1H), 7.1 (d, 2H), 7.2 (t, 1H), 7.4 (t, 2H), 7.6 (m, 4H), 7.8 (d, 2H), 8.3 (s, 1H), 8.8 (br s, 1H), 9.95 (br s, 1H) | 538, 540 |

[1] Chromatography and MS was carried out by LCMS on a Micromass OpenLynx system using System A:

EXAMPLE 23

2-(4-Sulphamoylanilino)-4-(2-cyanoanilino)-5-chloropyrimidine 2,5-Dichloro4-(2-cyanoanilino)pyrimidine (265 mg, 1.00 mmol) was dissolved in n-butanol (1 ml) and sulphanilamide (207 mg, 1.20 mmol) was added. The resulting suspension was heated at reflux for 2 hours and allowed to cool to ambient temperature. The reaction mixture was then basified using methanolic ammonia and evaporated onto silica. The residue was purified by column chromatography eluting with 0–15% 2.0M methanolic ammonia solution in dichloromethane to afford a solid product (42.6 mg). NMR (303.1K): 7.09 (2H, s), 7.41–7.59 (5H, m), 7.65 (1H, d), 7.74–7.86 (1H, m), 7.94 (1H, d 8.25 (1H, s), 9.46 (1H, s), 9.78 (1H, s); MS (M+H)$^+$: 401, 403.

EXAMPLES 24–28

The following compounds were prepared by an analogous method to that described in Example 23 using the appropriate 4-sulphonyl aniline.

| Ex | R$^4$ | R$^5$ | R$^2$ | R$^3$ | NMR, 400 MHz @ 373k | MS |
|---|---|---|---|---|---|---|
| 24 | Cl | H | 2-CN | 5-methyl-1,3,4-thiadiazol-2-ylamino | 2.46 (3H, s), 7.38–7.58 (6H, m), 7.79 (1H, t), 7.93 (1H, d), 8.25 (1H, s), 9.46 (1H, s), 9.80 (1H, s), 13.79 (1H, s) | 497, 499 (M − H) |
| 25 | Cl | H | 2-CN | N,N-bis(2-hydroxyethyl)amino | 3.09 (4H, t), 3.50 (4H, dt), 4.77 (1H, t), 7.46 (2H, d), 7.50 (1H, t), 7.55–7.68 (3H, m), 7.80 (1H, t), 7.94 (1H, d), 8.27 (1H, s), 9.47 (1H, s), 9.83 (1H, s) | 487, 489 (M − H) |
| 26 | Cl | 2-OMe | 2-CN | —NH$_2$ | 3.83 (3H, s), 7.08 (3H, m), 7.32–7.41 (1H, m), 7.49 (1H, dd), 7.65–7.71 (2H, m), 7.82 (1H, d), 7.98 (1H, s), 8.22 (1H, s), 8.30–8.35 (1H, m), 9.16 (1H, s) | 431, 433 (M + H) |
| 27 | Cl | H | 2-CN | thiazol-2-ylamino | 6.81 (1H, d), 7.22 (1H, d), 7.40–7.57 (5H, m), 7.62 (1H, d), 7.79 (1H, t), 7.91 (1H, d), 8.24 (1H, s), 9.45 (1H, s), 9.76 (1H, s), 12.57 (1H, s) | 484, 486 (M + H) |
| 28 | Cl | H | 2-CN | 3,4-dimethylisoxazol-5-ylamino | 1.60 (3H, s), 2.08 (3H, s), 7.39 (2H, d), 7.46–7.67 (4H, m), 7.79 (1H, t), 7.91 (1H, d), 8.28 (1H, s), 9.51 (1H, s), 9.91 (1H, s), 10.75 (1H, s) | 496, 498 (M + H) |

EXAMPLE 29

2,4-Di-(4-sulphamoylanilino)-5-bromopyrimidine

A solution of 5-bromo-2,4-dichloropyrimidine (228 mg, 1.0 mmol), 4-sulphanilamide (180 mg, 1.05 mmol) and N,N-diisopropylethylamine (174 μl 1.0 mmol) in n-butanol (30 ml) was heated at 100° C. for 16 hours. A gum formed out of solution. Diethyl ether (20 ml) was added, causing the gum to solidify, and further precipitation to occur. The solid was collected by filtration and triturated with hot methanol, giving the title product (55 mg) as a white solid. NMR: (s, 2H), 7.30 (s, 2H), 7.64 (d, 2H), 7.80 (m, 4H), 7.88 (d, 2H), 8.36 (s, 1H), 8.93 (s, 1H), 9.88 (s, 1H).

EXAMPLE 30

2-(3-Sulphamoylanilino)-4-[(2-morpholino)anilino]pyrimidine

In this example the operations were carried out using a Zymate XP robot with solution additions via a Zymate Master Laboratory Station and stirred in a Stem RS5000 Reacto-Station. The structure of the compound was confirmed by LCMS on a Micromass OpenLynx system using the System A.

To 3-aminobenzenesulphonamide (172 mg, 1.0 m.mol) in 1,4-dioxane (8 ml) was added 2-Chloro-4-[(2-Morpholino)anilino]pyrimidine (290 mgs, 1 m.mol) and hydrogen chloride (4.0M solution in 1,4-dioxane, 50 μl). The mixture was heated at 100° C. for 60 hrs. The reaction mixture was cooled, the resulting solid filtered, washed with 1,4-dixane and dried (in vacuo at 48° C.) to give pale brown solid (358 mg). Rt 5.88; MS (M+H)$^+$: 427.

EXAMPLE 31

2-(4-Sulphamoylanilino)-4-(4-methoxyphenoxy)-5-chloropyrimidine

A solution of 2,5 dichloro-4-(4-methoxyphenoxy)pyrimidine (Method 25; 0.65 g, 2.4 mmol) and sulphanilamide (0.38 g, 2.2 mmol) in NMP(1.5 ml) was heated to 100° C. for 4 hours. The reaction mixture was partitioned between water and ethyl acetate. The organic solution was evaporated and the residue purified by column chromatography eluting with 0.1% formic acid, 4% methanol in dichloromethane to afford a solid product (0.17 g, 19%). NMR: 3.81 (s, 3H), 7.05 (d, 2H), 7.10 (s, 2H), 7.22 (d, 2H), 7.50 (d, 4H), 8.50 (s, 1H), 10.6 (br s, 1H); MS [M–H]$^-$: 405, 407.

Preparation of Starting Materials

The starting materials for the examples above are either commercially available or are readily prepared by standard methods from known compounds. The following are methods used in the preparation of some of the starting materials used in the above reactions.

Method 1

2-Chloro-4-(2-fluoro-5-methyl(N-4,4,4-trifluorobuty)anilino)pyrimidine

2-Chloro-4-(2-fluoro-5-methylanilino)pyrimidine (750 mg, 3.16 mmol), 4,4,4-trifluoro-1-bromobutane (725 mg, 3.80 mmol) and potassium carbonate (525 mg, 3.80 mmol) were dissolved in N,N-Dimethylformamide (3 ml). The reaction mixture was stirred at room temperature for 12 hours and then evaporated onto silica (5 ml) and purified by column chromatography eluting with ethyl acetate (0–40%): isohexane, to yield a solid on evaporation (976 mg). NMR (373K): 1.79 (m, 2H), 2.28 (m, 2H), 2.33 (s, 3H), 3.91 (t, 2H), 6.19 (d, 1H), 7.28 (m, 3H), 8.03 (d, 1H); MS (M+H)$^+$: 347, 349.

Methods 2–10

The following compounds were prepared by an analogous method to that described in Method 1 using the appropriate 2-chloro-4-anilinopyrimidine and the relevant alkylating agent.

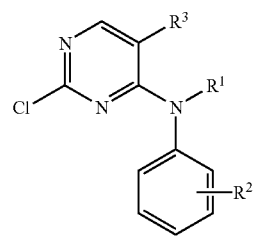

| Method | R$^1$ | R$^2$ | R$^3$ | MS (M + H)$^+$ |
|---|---|---|---|---|
| 2 | —CH$_2$CH$_2$CH$_2$CF$_3$ | 4-Br | H | 393, 395[1] |
| 3 | —CH$_2$CH=CHBr | 4-Br | H | 401, 403, 405[1] |
| 4 | —CH$_2$CH=CHPh | 4-Br | H | 400.2, 402.2 |
| 5 | —CH$_2$CH=CHBr | 2-F, 5-CH$_3$ | H | 355, 357[1] |
| 6 | —CH$_2$CH=CHPh | 2-F, 5-CH$_3$ | H | 354.3, 356.3 |
| 7 | —CH$_2$CH$_2$CH$_2$CF$_3$ | 2-CN | H | 340[1] |
| 8 | —CH$_2$CH=CHBr | 2-CN | H | 348, 350, 352[1] |
| 9 | —CH$_2$CH=CHPh | 2-CN | H | 347.2, 349.3 |
| 10 | —CH$_2$CH=CHPh | 2-F, 5-CH$_3$ | Cl | 388.3, 390.3 |

[1] where the mass shown is an M$^{+\cdot}$

Method 11

Chloro-4-(2-cyanoanilino)pyrimidine 2,4-Dichloropyrimidine (3 g, 0.02 mol), anthranilonitrile (2.38 g, 0.02 mol) and concentrated hydrochloric acid (cat. amount) were added to water (5 ml). The reaction mixture was warmed to 40° C. to dissolve the starting materials and the resulting solution was stirred at room temperature for 12 hours. The solid precipitate that had formed was collected filtration and dried in vacuo to yield a pale yellow solid (5.14 g). NMR: 6.78 (d, 1H), 7.39 (t, 1H), 7.61 (d, 1H), 7.71 (t, 1H), 7.85 (d, 1H), 8.20 (d, 1H), 10.22 (br s, 1H); MS (M+H)$^+$: 231.1, 233.1.

Method 12

2-Chloro-4-(4-bromoanilino)pyrimidine 2,4-Dichloropynrmidine (3 g, 20.14 mmol), 4-bromoaniline (3.46 g, 20.14 mmol) and di-isopropylethylamine (3.86 ml, 22.15 mmol) were dissolved in n-butanol (5 ml). The reaction mixture was heated at 120° C. for 12 hours, cooled and evaporated onto silica (5 ml). The residue was purified by column chromatography and eluted with ethyl acetate (50%):isohexane to yield a solid on evaporation (4.77 g). NMR: 6.74 (d, 1H), 7.55 (m, 4H), 8.16 (d, 1H), 10.09 (br s, 1H); MS (M+H)$^+$: 284.1, 286.1, 288.0.

Methods 13–17

The following compounds were prepared by an analogous method to that described in Method 12 using the appropriate 2,4-dichloropyrimidine and the relevant aniline.

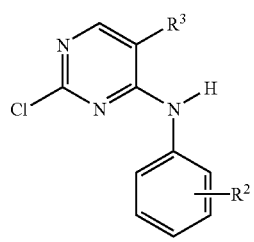

| Method | R[2] | R[3] | NMR, 400 MHz | MS (M + H)[+] |
|---|---|---|---|---|
| 13 | 2-F, 5-CH$_3$ | H | | 238.1, 240.1 |
| 14 | 2-F, 5-CH$_3$ | Cl | 2.29 (s, 3H), 7.17 (m, 3H), 8.35 (s, 1H), 9.49 (s, 1H) | |
| 15 | H | Br | | 282.1, 284.1, 286.1 |
| 16 | 2-CN | Cl | | 265.1, 267.1 |
| 17 | 2-(4-methylpiperazin... morpholine) | H | | 291, 293 |

Method 18

4-[2-(N,N-Diethylamino)ethylamino]benzenesulfonamide

The above starting material was prepared as described in Therapie, 1965, 20 (4), p.917–29.

Method 19

2,4,5-Trichloropyrimidine

5-Chlorouracil (10.0 g, 68.5 mmol) was dissolved in phosphorus oxychloride (60 ml) and phosphorus pentachloride (16.0 g, 77 mmol) was added. The reaction mixture was then stirred at reflux (110° C.) for 16 hrs then allowed to cool to 20° C. The reaction mixture was then poured slowly and carefully into water (200 ml) at 25° C. with vigorous stirring. Then stirred well for 90 minutes before addition of EtOAc (250 ml). Organic layer separated off and aqueous layer re-extracted into EtOAc (250 ml). The organic layers were then combined and washed with sodium bicarbonate (200 ml aqueous solution), brine (200 ml) and then evaporated to a yellow liquid. The crude material was purified by column chromatography eluting with dichloromethane to afford the product as a yellow liquid (6.37 g, 51%). NMR (CDCl$_3$): 8.62 (s, 1H); MS (M+): 182, 184,186.

Method 20

4-[2-Hydroxy-3-(dimethylamino)propoxy]aniline hydrochloride

A solution of 4-[2-hydroxy-3-(dimethylamino)propoxy]nitrobenzene (Method 21, 3.75 g) in ethanol (40 ml) was catalytically hydrogenated over 10% palladium-on-carbon (0.4 g) overnight. The catalyst was removed by filtration through diatomaceous earth and the filtrate was concentrated. The residue was dissolved in diethyl ether containing a small amount of isopropanol and ethereal hydrogen chloride (1M, 16 ml) was added. Diethyl ether was removed by evaporation and the solid residue was suspended in isopropanol. The mixture was heated on a steam bath for several minutes and then allowed to cool. The insoluble solid was collected by filtration, washed with isopropanol and ether, and dried to give the product (3.04 g, 72.4%). NMR: 2.80 (s, 6H), 3.15 (m, 2H), 3.88 (m, 2H), 4.25 (m, 1H), 5.93 (br S, 1H), 6.88 (m, 4H); MS (M+H)[+]: 211; $C_{11}H_{18}N_2O_2$.1.6 HCl requires: C; 49.2, H; 7.4, N; 10.4, Cl; 21.7%; found: C; 49.2, H; 7.2, N; 10.1; Cl; 19.1%.

Method 21

4-[2-Hydroxy-3-(dimethylamino)propoxy]nitrobenzene 4-(2,3-Epoxypropoxy)nitrobenzene (obtained as described in Synthetic Communications, 1994, 24, 833; 4.3 g,) was dissolved in methanol (30 ml) and DMF (10 ml). A solution of dimethylamine in methanol (2M, 17 ml) was added and the mixture was stirred overnight. Volatile material was removed by evaporation and the residue was partitioned between saturated sodium bicarbonate (100 ml) and ethyl acetate (100 ml). The organic layer was separated and washed with saturated sodium chloride (2×100 ml) and dried (MgSO$_4$). Concentration gave the product as an oil that slowly crystallised under high vacuum (4.79 g, 89.9%). NMR (CDCl$_3$): 2.33 (s, 6H), 2.98 (m, 1H), 2.54 (m, 1H), 4.00 (m, 3H), 7.00 (d, 2H), 8.20 (d, 2H); MS (M+H)[+]: 241.

Method 22

4-{2-[(N-Methyl-N-phenyl)amino]ethylsulphonyl}aniline

To a solution of 4-{2-[(N-methyl-N-phenyl)amino]ethylsulphonyl}nitrobenzene (Method 23; 10 g, 31.25 mmol) in ethanol (100 ml) was added 5 ml of water, 1 ml HCl (conc.) and 25 g of iron pin dust. The reaction was heated at reflux for 3 hours. The reaction was cooled, basified by the addition of caustic and filtered. The iron residue was extracted with a further 100 ml of boiling ethanol and filtered again. To the combined filtrates was added water (400 ml), the product was collected by filtration. The crude material was dissolved in acetone (80 ml) treated with charcoal, filtered and precipitated by the addition of water. The product was collected by filtration. (6 g). Mp 158–159° C.; NMR: 2.8 (s, 3H), 3.2 (m, 2H), 3.5 (m, 2H), 6.1 (s, 2H), 6.5 (d, 2H), 6.6 (m. 3H), 7.1 (t, 2H), 7.5 (d, 2H); MS (M+H)[+]:291

Method 23

4-{2-[(N-Methyl-N-phenyl)amino]ethylsulphonyl}nitrobenzene

To a solution of 1-[(2-chloroethyl)sulphonyl]-4-nitrobenzene (U.S. Pat. No. 5,716,936; 5 g, 22.8 mmol) in water (50 ml) was added sodium acetate (3 g, 36.6 mmol) and N-methylaniline (3.3 g, 30.8 mmol). The reaction was heated to reflux for 1 hour. After cooling briefly, the hot aqueous supernatant was decanted. The residual oil was washed with cold water. The resulting solid was collected by filtration and air dried. The crude material was recrystallized from benzene/petroleum ether to give red crystals (5.3 g). Mp 111–113° C. This material was used without further characterisation.

Method 24

4-[(2-[N-Morpholino]ethyl)sulphonyl]aniline

The title compound can be prepared by a method analogous to that used in Method 22 above (parts A-C) using morpholine in place of N-methylaniline. NMR: 2.2 (m, 4H), 3.3 (m, 4H), 3.4 (m, 4H), 6.05 (br s, 2H), 6.6 (d, 2H), 7.4 (d, 2H); MS (M+H)$^+$: 271.

Method 25

2,5-Dichloro-4-(4-methoxyphenoxy)pyrimidine

A solution of 2,4,5-trichloropyrimidine (1.0 g, 5.4 mmol) and 4-methoxyphenol (0.64 g, 5.2 mmol) in NMP (2.5 ml) was treated with anhydrous potassium carbonate (1.65 g, 12 mmol). The reaction mixture was allowed to stir at ambient temperature for 18 hours. The reaction was partitioned between water and ethyl acetate. The organic layer was evaporated and the residue purified by column chromatography eluting with 10% ethyl acetate in isohexane to afford a solid product (1.33 g, 90%). NMR: 3.78 (s, 3H), 7.00 (d, 2H), 7.20 (d, 2H), 8.77 (s, 1H); MS (M+H)$^+$271, 273.

EXAMPLE 32

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

| (e): Injection I | (50 mg/ml) |
|---|---|
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1 M Sodium hydroxide solution | 15.0% v/v |
| Water for injection | to 100% |

| (g): Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note

The above formulations may be obtained by conventional procedures well known in the pharmaceutical art. The tablets (a)–(c) may be enteric coated by conventional means, for example to provide a coating of cellulose acetate phthalate.

The invention claimed is:

1. A pyrimidine derivative of the formula (I):

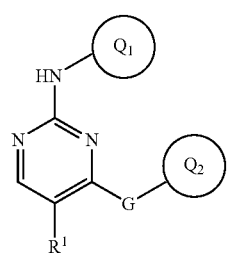

(I)

wherein:

Q$_1$ and Q$_2$ are independently selected from aryl or carbon linked heteroaryl; and Q$_1$ is substituted on a ring carbon by a sulphamoyl group, or one of Q$_1$ and Q$_2$ or both Q$_1$ and Q$_2$ is substituted on a ring carbon by one group selected from N—(C$_{1-4}$alkyl)sulphamoyl (optionally substituted by halo or hydroxy), N,N-di-(C$_{1-4}$alkyl) sulphamoyl (optionally substituted by halo or hydroxy), C$_{1-4}$alkylsulphonyl (optionally substituted by halo or hydroxy) or a substituent of the formula (Ia) or (Ia'):

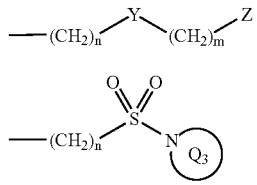

(Ia)

(Ia')

wherein:
Y is —NHS(O)$_2$—, —S(O)$_2$NH— or —S(O)$_2$—;
Z is R$^a$O—, R$^b$R$^c$N—, R$^d$S—, R$^e$R$^f$NNR$^g$—, C$_{3-8}$cycloalkyl, phenyl or a heteroc wherein said phenyl, C$_{3-8}$cycloalkyl or heterocyclic group are optionally substituted on a rig carbon by one or more groups selected from R$^h$; and wherein if said heterocyclic group contains an —NH— moiety that nitrogen may be optionally substituted by a group selected from R$^i$;
R$^a$, R$^b$, R$^c$, R$^d$, R$^e$, R$^f$ and R$^g$ are independently selected from hydrogen, C$_{1-4}$alkyl, C$_{2-4}$alkenyl, phenyl, heterocyclic group and C$_{3-8}$cycloalkyl; wherein said C$_{1-4}$alkyl, C$_{2-4}$alkenyl and C$_{3-8}$cycloalkyl are optionally substituted by one or more groups selected from R$^j$;
n is 0 or 1;
m is 1, 2 or 3, in addition m may be 0 when Z is C$_{3-8}$cycloalkyl, phenyl or a heterocyclic group;
Q$_3$ is a nitrogen linked heterocycle; wherein said heterocycle is optionally substituted on a ring carbon by one or more groups selected from R$^k$; and wherein if said heterocyclic group contains an —NH— moiety that nitrogen may be optionally substituted by a group selected from R$^m$
G is —O—, —S— or —NR$^2$—;
R$^2$ is selected from hydrogen, C$_{1-6}$alkyl, C$_{3-6}$alkenyl and C$_{3-6}$alkynyl; wherein said C$_{1-6}$alkyl, C$_{3-6}$alkenyl and C$_{3-6}$alkynyl are optionally substituted by one or more groups selected from R$^n$;
R$^1$ is selected from hydrogen, halo, hydroxy, amino, N—(C$_{1-3}$alkyl)amino, N,N-di-(C$_{1-3}$alkyl)amino, cyano, trifluoromethyl, trichloromethyl, C$_{1-3}$alkyl [optionally substituted by 1 or 2 substituents independently selected from halo, cyano, amino, N—(C$_{1-3}$alkyl)amino, N,N-di-(C$_{1-3}$alkyl)amino, hydroxy and trifluoromethyl], C$_{3-5}$alkenyl [optionally substituted by up to three halo substituents, or by one trifluoromethyl substituent], C$_{3-5}$alkynyl, C$_{1-3}$alkoxy, mercapto, C$_{1-3}$alkylsulphanyl, carboxy and C$_{1-3}$alkoxycarbonyl;
Q$_1$ is optionally substituted on a ring carbon by one to four substituents independently selected from halo, mercapto, nitro, formyl, formamido, carboxy, cyano, amino, ureido, carbamoyl, C$_{1-4}$alkyl, C$_{2-4}$alkenyl, C$_{2-4}$alkynyl [wherein said C$_{1-4}$alkyl, C$_{2-4}$alkenyl and C$_{2-4}$alkynyl are optionally substituted by one or more groups selected from R$^o$], C$_{1-4}$alkanoyl, C$_{1-4}$alkoxycarbonyl, heterocyclic group, C$_{1-4}$alkylS(O)$_a$ wherein a is 0 or 1 [optionally substituted by hydroxy], N'—(C$_{1-4}$alkyl)ureido, N',N'-di-(C$_{1-4}$alkyl)ureido, N'—(C$_{1-4}$alkyl)ureido, N',N'-di-(C$_{1-4}$alkyl)-N—(C$_{1-4}$alkyl)ureido, N—C$_{1-4}$alkylamino, N,N-di-(C$_{1-4}$alkyl)amino, N—C$_{1-4}$alkylcarbamoyl, N,N-di-(C$_{1-4}$alkyl)carbamoyl and C$_{1-4}$alkanoylamino;

and also independently, or in addition to, the above substituents, Q$_1$ may be optionally substituted by one to two substituents independently selected from aryl, C$_{3-8}$cycloalkyl and a heterocyclic group; wherein said aryl, C$_{3-8}$cycloalkyl or heterocyclic group may be optionally substituted on a ring carbon by one or more groups selected from R$^p$; and wherein if said heterocyclic group contains an —NH— moiety that nitrogen may be optionally substituted by a group selected from R$^q$;
and also independently, or in addition to, the above substituents, Q$_1$ may be optionally substituted by one C$_{1-4}$alkoxy or by one hydroxy substituent;
Q$_2$ is optionally substituted on a ring carbon by one to four substituents independently selected from halo, hydroxy, mercapto, nitro, formyl, formamido, carboxy, cyano, amino, ureido, carbamoyl, C$_{1-4}$alkyl, C$_{2-4}$alkenyl, C$_{2-4}$alkynyl, C$_{1-4}$alkoxy [wherein said C$_{1-4}$alkyl, C$_{2-4}$alkenyl, C$_{2-4}$alkynyl and C$_{1-4}$alkoxy are optionally substituted by one or more groups selected from R$^1$], C$_{1-4}$alkanoyl, C$_{1-4}$alkoxycarbonyl, heterocyclic group, C$_{1-4}$alkylS(O)$_a$ wherein a is 0 or 1 [optionally substituted by hydroxy], N'—(C$_{1-4}$alkyl)ureido, N',N'-di-(C$_{1-4}$alkyl)ureido, N'—(C$_{1-4}$alkyl)-N—(C$_{1-4}$alkyl)ureido, N',N',-di-(C$_{1-4}$alkyl)-N—(C$_{1-4}$alkyl)ureido, N—C$_{1-4}$alkylamino, N,N-di-(C$_{1-4}$alkyl)amino, N—C$_{1-4}$alkylcarbamoyl, N,N-di-(C$_{1-4}$alkyl)carbamoyl, C$_{1-4}$alkenyloxy, C$_{2-4}$alkynyloxy and C$_{1-4}$alkanoylamino;
and also independently, or in addition to, the above substituents, Q$_2$ may be optionally substituted by one to two substituents independently selected from aryl, C$_{3-8}$cycloalkyl or a heterocyclic group; wherein said aryl, C$_{3-8}$cycloalkyl or heterocyclic group may be optionally substituted on a ring carbon by one or more groups selected from R$^s$; and wherein if said heterocyclic group contains an —NH— moiety that nitrogen may be optionally substituted by a group selected from R$^t$;
R$^j$, R$^n$, R$^o$ and R$^r$ are independently selected from hydroxy, halo, amino, cyano, formyl, formamido, carboxy, nitro, mercapto, carbamoyl, sulphamoyl, N—C$_{1-4}$alkylamino, N,N-di-(C$_{1-4}$alkyl)amino, C$_{1-4}$alkanoyl, C$_{1-4}$alkanoyloxy, C$_{1-4}$alkoxy, C$_{1-4}$alkoxycarbonyl, N—C$_{1-4}$alkylcarbamoyl, N,N-di-(C$_{1-4}$alkyl)carbamoyl, C$_{1-4}$alkanoylamino, C$_{1-4}$alkylS(O)$_a$ wherein a is 0 to 2, C$_{1-4}$alkylsulphonylamino, N—(C$_{1-4}$alkyl)sulphamoyl, N—(C$_{1-4}$alkyl)$_2$sulphamoyl, N—(C$_{1-4}$alkyl)carbamoyl, N—(C$_{1-4}$alkyl)$_2$carbamoyl, phenyl, phenylthio, phenoxy, C$_{3-8}$cycloalkyl and a heterocyclic group; wherein said phenyl, phenylthio, phenoxy, C$_{3-8}$cycloalkyl or heterocyclic group may be optionally substituted on a ring carbon by one or more groups selected from R$^u$; and wherein if said heterocyclic group contains an —NH— moiety that nitrogen may be optionally substituted by a group selected from R$^v$;
R$^h$, R$^k$, R$^p$ R$^s$ and R$^u$ are independently selected from hydroxy, halo, amino, cyano, formyl, formamido, carboxy, nitro, mercapto, carbamoyl, sulphamoyl, C$_{1-4}$alkyl [optionally substituted by one or more groups selected from halo, cyano, amino, N—C$_{1-4}$alkylamino, N,N-di-(C$_{1-4}$alkyl)amino or hydroxy], C$_{2-4}$alkenyl [optionally substituted by one or more groups selected from halo], C$_{2-4}$alkynyl, N—C$_{1-4}$alkylamino, N,N-di-(C$_{1-4}$alkyl)amino, C$_{1-4}$alkanoyl, C$_{1-4}$alkanoyloxy, C$_{1-4}$alkoxy [optionally substituted by one or more groups selected from halo], C$_{1-4}$alkoxycarbonyl, N—$C_{1-4}$alkylcarbamoyl, N,N-di-($C_{1-4}$alkyl)carbamoyl, $C_{1-4}$alkanoylamino, $C_{1-4}$alkylS(O)$_a$ wherein a is 0 to 2, $C_{1-4}$alkylsulphonylamino, N—($C_{1-4}$alkyl)sulphamoyl, N—($C_{1-4}$alkyl)$_2$sulphamoyl, phenyl, $C_{3-8}$cycloalkyl and a heterocyclic group; and R$^t$, R$^q$, R$^t$ and R$^v$ are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl;

or a pharmaceutically acceptable salt or in vivo hydrolysable ester formed from an available carboxy or hydroxy group thereof.

2. A pyrimidine compound as claimed in claim 1 wherein $Q_1$ is phenyl or a pharmaceutically acceptable salt or in vivo hydrolysable ester formed from an available carboxy or hydroxy group thereof.

3. A pyrimidine compound as claimed in claims 1 wherein $Q_2$ is phenyl or a pharmaceutically acceptable salt or in vivo hydrolysable ester formed from an available carboxy or hydroxy group thereof.

4. A pyrimidine compound as claimed in claims 1 wherein $Q_1$ is substituted on a ring carbon by sulphamoyl group or one of $Q_1$ and $Q_2$ or both of $Q_1$ and $Q_2$ are substituted on a ring carbon by one group selected from mesyl, N-(2-diethylaminoethyl)sulphamoyl, 2-(N-methyl-N-phenylamino)ethylsulphonyl, 2-morpholinoethylsulphonyl, N-(5-methylthiadiazol-2-yl)sulphamoyl, N,N-di-(2-hydroxyethyl)sulphamoyl, N-(thiazol-2-yl)sulphamoyl, N-(3,4-dimethylisoxazol-5-yl)sulphamoyl, N-(pyrid-2-yl)sulphamoyl and N-methylsulphamoyl or a pharmaceutically acceptable salt or in vivo hydrolysable ester formed from an available carboxy or hydroxy group thereof.

5. A pyrimidine compound as claimed in claims 1 wherein $Q_1$ is phenyl substituted in the para- or meta-position relative to the —NH— by sulphamoyl, N—($C_{1-4}$alkyl)sulphamoyl (optionally substituted by halo or hydroxy), N,N-di-($C_{1-4}$alkyl)sulphamoyl (optionally substituted by halo or hydroxy), $C_{1-4}$alkylsulphonyl (optionally substituted by halo or hydroxy) or a substituent of the formula (Ia) or (Ia') or a pharmaceutically acceptable salt or in vivo hydrolysable ester formed from an available carboxy or hydroxy group thereof.

6. A pyrimidine compound as claimed in claims 1 wherein G is —O—, —NH—, (4,4,4-trifluorobutyl)N—, -(3-bromo-2-propenyl) N— or -(3-phenyl-2-propenyl)N— or a pharmaceutically acceptable salt or in vivo hydrolysable ester formed from an available carboxy or hydroxy group thereof.

7. A pyrimidine compound as claimed in claims 1 wherein R$^1$ is hydrogen or halo or a pharmaceutically acceptable salt or in vivo hydrolysable ester formed from an available carboxy or hydroxy group thereof.

8. A pyrimidine compound as claimed in claims 1 wherein $Q_1$ is optionally substituted by one $C_{1-4}$alkoxy substituent or a pharmaceutically acceptable salt or in vivo hydrolysable ester formed from an available carboxy or hydroxy group thereof.

9. A pyrimidine compound as claimed in claims 1 wherein $Q_2$ is optionally substituted on a ring carbon by one to two substituents independently selected from halo, cyano, methyl, methoxy and morpholino or a pharmaceutically acceptable salt or in vivo hydrolysable ester formed from an available carboxy or hydroxy group thereof.

10. A pyrimidine compound as claimed in claims 1 selected from:
  2-(4sulphamoylanilino)-4-(2-cyanoanilino)pyrimidine;
  2-(4-N-methylsulphamoylanilino)-4-anilino-5-bromopyrimidine;
  2-(4-sulphamoylanilino)-4-anilino-5-bromopyrimidine;
  2-(4sulphamoylanilino)-4-(4-methoxyphenoxy)-5-chloropyrimidine;

or pharmaceutically acceptable salt or in vivo hydrolysable ester formed from an available carboxy or hydroxy group thereof.

11. A process for preparing a pyrimidine compound, or pharmaceutically acceptable salt or in vivo hydrolysable ester formed from an available carboxy or hydroxy group thereof, as claimed in claims 1 which comprises of:
  a) for compounds of formula (I) where G is —NR$^2$—; reacting a pyrimidine of formula (II):

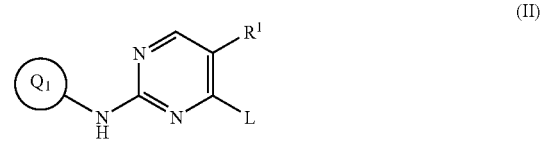

(II)

wherein L is a displaceable group as defined below, with a compound of formula (III):

(III)

where G is —NR$^2$—;
  b) reaction of a pyrimidine of formula (IV):

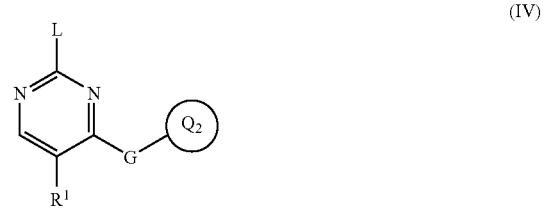

(IV)

wherein L is a displaceable group as defined below, with a compound of formula (V):

(V)

c) for compounds of formula (I) wherein the sidechain is of formula (Ia) and Y is —S(O)$_2$NH—; by reaction of a compound of formula (VI):

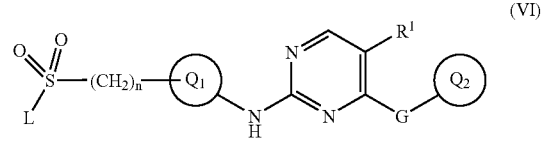

(VI)

where L is a displaceable group; with an amine of formula (VII):

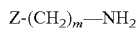   (VII)

d) for compounds of formula (I) wherein the sidechain is of formula (Ia) and Y is —NHS(O)$_2$— by reaction of an amine of formula (VIII):

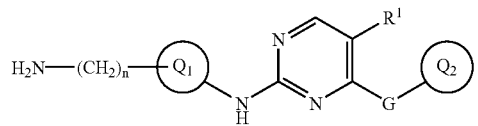   (VIII)

with a compound of formula (IX):

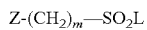   (IX)

where L is a displaceable group;

e) for compounds of formula (I) wherein the sidechain is of formula (Ia'); by reaction of a compound of formula (VI) with an amine of formula (X):

   (X)

and thereafter optionally:
   i) converting a compound of the formula (I) into another compound of the formula (I);
   ii) removing any protecting groups;
   iii) forming a pharmaceutically acceptable salt or in vivo hydrolysable ester formed from an available carboxy or hydroxy group thereof.

12. A pharmaceutical composition which comprises a pyrimidine compound of formula (I), or a pharmaceutically acceptable salt or in vivo hydrolysable ester formed from an available carboxy or hydroxy group thereof, as claimed in any one of claims 1 to 10, in association with a pharmaceutically acceptable diluent or carrier.

* * * * *